US012591970B2

(12) United States Patent
Wang et al.

(10) Patent No.: US 12,591,970 B2
(45) Date of Patent: Mar. 31, 2026

(54) METHODS AND SYSTEMS FOR DETERMINING HEMODYNAMIC PARAMETERS

(71) Applicant: SHANGHAI UNITED IMAGING HEALTHCARE CO., LTD., Shanghai (CN)

(72) Inventors: Xiaodong Wang, Shanghai (CN); Jian Guo, Shanghai (CN); Peiming Qin, Shanghai (CN); Deyuan Kong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 287 days.

(21) Appl. No.: 18/401,378

(22) Filed: Dec. 30, 2023

(65) Prior Publication Data

US 2024/0221156 A1      Jul. 4, 2024

(30) Foreign Application Priority Data

Dec. 30, 2022      (CN) .......................... 202211738649.4

(51) Int. Cl.
G06T 7/00              (2017.01)
A61B 5/02              (2006.01)
(52) U.S. Cl.
CPC ........ G06T 7/0012 (2013.01); A61B 5/02028 (2013.01); G06T 2207/30104 (2013.01)

(58) Field of Classification Search
CPC ......... G06T 7/0012; G06T 2207/30104; A61B 5/02028
See application file for complete search history.

(56) References Cited

U.S. PATENT DOCUMENTS

| 2014/0249399 | A1 | 9/2014 | Sharma et al. |
| 2015/0051888 | A1 | 2/2015 | Itu et al. |
| 2017/0068797 | A1* | 3/2017 | Sharma ................ A61B 5/0263 |
| 2024/0169540 | A1* | 5/2024 | Bouwman ................ G06T 7/10 |

* cited by examiner

*Primary Examiner* — Casey L Kretzer
(74) *Attorney, Agent, or Firm* — METIS IP LLC

(57)      ABSTRACT

Some embodiments of the present disclosure provide methods and systems for determining a hemodynamic parameter. The method may include: obtaining image data of a subject being acquired in a rest state; obtaining a trained machine learning model; and determining, based on the trained machine learning model, at least one target hemodynamic parameter of the subject. The trained machine learning model may be obtained based on multiple sets of sample image data. Each set of the multiple sets of sample image data may include a first image data and at least one of a second image data or a third image data. The first image data may be acquired in a rest state of a first sample subject, the second image data may be acquired in a hyperemic state of the first sample subject, and the third image data may be acquired in a hyperemic state of a second sample subject including the first sample subject.

20 Claims, 12 Drawing Sheets

<u>200</u>

500

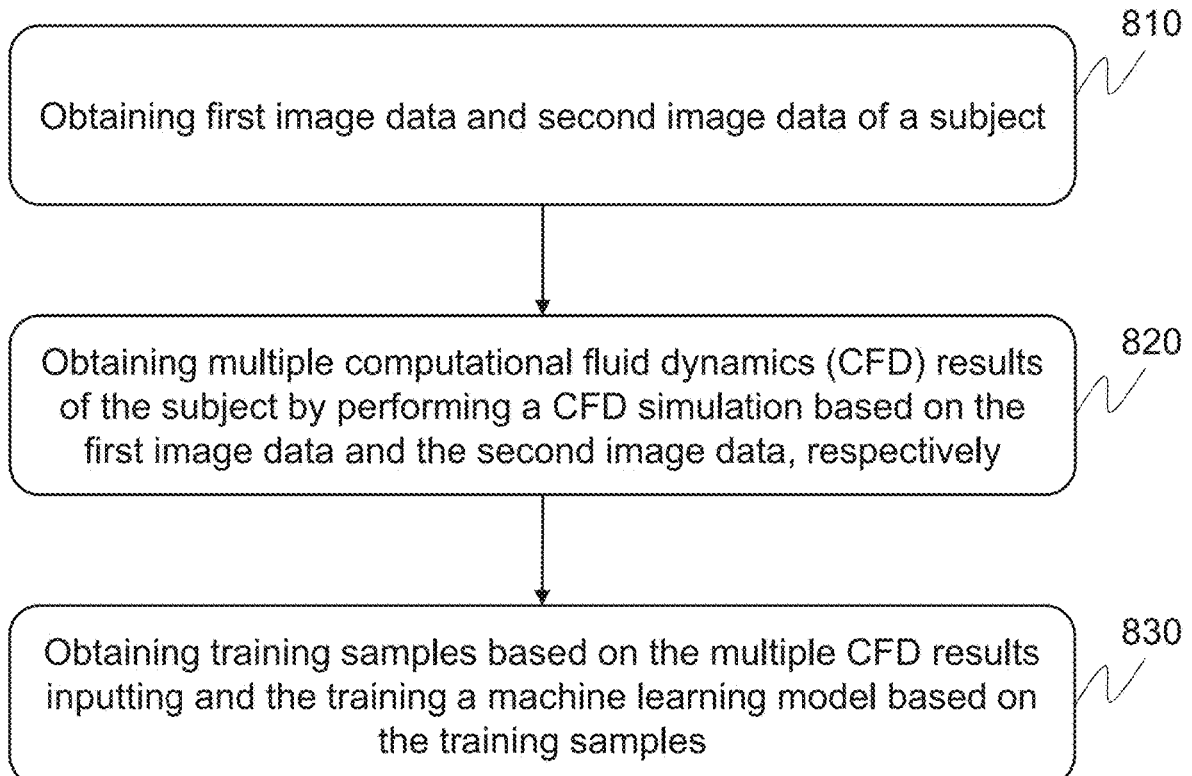

<u>800</u>

810

Obtaining first image data and second image data of a subject

820

Obtaining multiple computational fluid dynamics (CFD) results of the subject by performing a CFD simulation based on the first image data and the second image data, respectively

830

Obtaining training samples based on the multiple CFD results inputting and the training a machine learning model based on the training samples

FIG.8

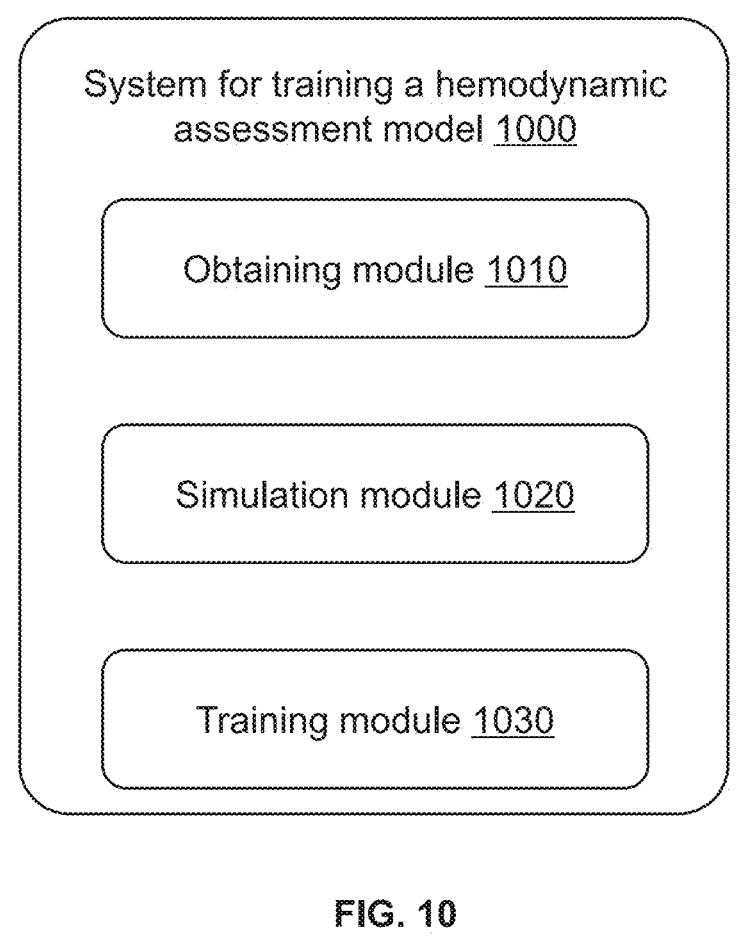

System for training a hemodynamic
assessment model 1000

Obtaining module 1010

Simulation module 1020

Training module 1030

FIG. 10

METHODS AND SYSTEMS FOR DETERMINING HEMODYNAMIC PARAMETERS

CROSS-REFERENCE TO RELATED APPLICATIONS

This application claims priority to Chinese Patent Application No. 202211738649.4, filed Dec. 30, 2022, the contents of which are entirely incorporated herein by reference.

TECHNICAL FIELD

The present disclosure relates to the field of blood flow assessment, and in particular, to methods and systems for determining a hemodynamic parameter.

BACKGROUND

Hemodynamic parameters of coronary arteries are critical for determining an ischemic state of the heart. For example, a fractional flow reserve (FFR) of the coronary artery is a good indicator for determining whether the coronary artery is ischemic or not. An existing assessment manner mainly obtains the hemodynamic parameters of blood flow based on a CTA (computed tomography angiography) image in a rest state. However, this manner suffers from high sensitivity to masks, low fault tolerance for plaque and stenosis identification, and long computational time.

Therefore, it is desirable to provide methods and systems for determining a hemodynamic parameter based on image data of a subject in a rest state quickly and accurately while considering information of the subject in a hyperemic state.

SUMMARY

One of the embodiments of the present disclosure provides a system for determining hemodynamic parameters. The system may include at least one storage medium including a set of instructions, and at least one processor in communication with the at least one storage medium. When executing the set of instructions, the at least one processor may be directed to cause the system to perform operations including obtaining image data of a subject being acquired in a rest state; obtaining a trained machine learning model; and determining, based on the trained machine learning model, at least one target hemodynamic parameter of the subject. The trained machine learning model may be obtained based on multiple sets of sample image data. Each set of the multiple sets of sample image data may include a first image data and at least one of a second image data or a third image data. The first image data may be acquired in a rest state of a first sample subject, the second image data may be acquired in a hyperemic state of the first sample subject, and the third image data may be acquired in a hyperemic state of a second sample subject associated with the first sample subject.

In some embodiments, the processor may be further configured to determine, based on the image data of the subject, a structure model of the subject; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject; determine one or more boundary conditions associated with the subject; and determine the at least one target hemodynamic parameter of the subject by inputting, the structure model, and the one or more boundary conditions into the trained machine learning model.

In some embodiments, the processor may be further configured to determine the at least one target hemodynamic parameter of the subject by inputting the image data of the subject into the trained machine learning model; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject.

In some embodiments, the trained machine learning model is obtained based on multiple groups of training samples, training samples in each group are determined based on one set of the multiple sets of sample image data, a training sample in each group includes a computational fluid dynamics (CFD) result determined based on the first image data, or the second image data, or the third image data and the first image data, or the third image data and the second image data, and a reference hemodynamic parameter corresponding to the CFD result.

In some embodiments, training samples in each group may include a first sample and at least one of a second sample, a third sample, or a fourth sample. The first sample may include a first CFD result determined based on the first image data. The second sample may include a second CFD result determined based on the second image data. The third sample may include a third CFD result determined based on the first image data and the third image data. The fourth sample may include a fourth CFD result determined based on the second image data and the third image data.

In some embodiments, the first sample is obtained according to operations including: determine, based on the first image data, a first structure model representing the first sample subject; determine, based on the first structure model, one or more first boundary conditions of the first sample subject; and determine, based on the one or more first boundary conditions and the first structure model, the first CFD result.

In some embodiments, the second sample is obtained according to operations including: determine, based on the second image data, a second structure model representing the first sample subject; determine, based on the second structure model or the second image data, one or more second boundary conditions of the first sample subject; and determine, based on the one or more second boundary conditions and the second structure model, the second CFD result.

In some embodiments, the determining, based on the second image data, a second structure model representing the first sample subject includes: obtain a second trained machine learning model; and determine the second structure model representing the first sample subject in the hyperemic state using the second trained machine learning model.

In some embodiments, the third sample is obtained according to operations including: determine, based on the first image data, a first structure model representing the first sample subject; determine, based on the third image data, one or more third boundary conditions of the first sample subject; and determine, based on the one or more third boundary conditions and the first structure model, the third CFD result.

In some embodiments, the fourth sample is obtained according to operations including: determine, based on the second image data, a second structure model representing the first sample subject; determine, based on the third image data, one or more third boundary conditions of the first sample subject; and determine, based on the one or more third boundary conditions and the second structure model, the fourth CFD result.

In some embodiments, the determining, based on the third image data, one or more third boundary conditions of the first sample subject includes: determine a first region from the first image data; determine a parametric image representing functional indexes of different portions of the first sample subject based on the third image data; determining a second region in the first region from the parametric image by registering the parametric image with the first image data; and determine, based on the second region, the one or more third boundary conditions.

In some embodiments, the processor may be further configured to, for one of the second sample and the fourth sample, register the second image data with the first image data to obtain a deformation field; and obtain the one of the second sample and the fourth image based on the deformation field.

One of the embodiments of the present disclosure provides a method for determining hemodynamic parameters. The method may be implemented on a computing apparatus. The computing apparatus may include at least one processor and at least one storage device. The method may include: obtaining image data of a subject being acquired in a rest state; obtaining a trained machine learning model; and determining, based on the trained machine learning model, at least one target hemodynamic parameter of the subject. The trained machine learning model may be obtained based on multiple sets of sample image data. Each set of the multiple sets of image data may include a first image data and at least one of a second image data or a third image data. The first image data may be acquired in a rest state of a first sample subject, the second image data may be acquired in a hyperemic state of the first sample subject, and the third image data may be acquired in a hyperemic state of a second sample subject associated with the first sample subject.

One or more embodiments of the present disclosure provide a non-transitory computer readable medium including a set of instructions. When executed by at least one processor, the set of instructions may direct the at least one processor to perform acts of: obtaining image data of a subject being acquired in a rest state; obtaining a trained machine learning model; and determining, based on the trained machine learning model, at least one target hemodynamic parameter of the subject. The trained machine learning model may be obtained based on multiple sets of sample image data. Each set of the multiple sets of image data may include a first image data and at least one of a second image data or a third image data. The first image data may be acquired in a rest state of a first sample subject, the second image data may be acquired in a hyperemic state of the first sample subject, and the third image data may be acquired in a hyperemic state of a second sample subject associated with the first sample subject.

The present disclosure may include at least the following beneficial effect. In the method for determining a hemodynamic parameter provided by the present disclosure, the vascular morphology in two states may be obtained by performing modeling of the coronary artery CTA blood vessels based on the CTA images scanned in two states of the rest state and the hyperemic state. The hyperemic state of the coronary artery may be more accurately obtained than a manner that relies merely on the CTA image in the single rest state. The values obtained from the more accurate CTA model in the hyperemic state may be all used as inputs of the neural network, which may make the neural network obtain more comprehensive information.

BRIEF DESCRIPTION OF THE DRAWINGS

The present disclosure is further illustrated in terms of exemplary embodiments. These exemplary embodiments are described in detail with reference to the drawings, wherein:

FIG. 8 is a flowchart illustrating an exemplary process for training a hemodynamic assessment model according to some embodiments of the present disclosure;

FIG. 10 is an exemplary schematic diagram illustrating a system for training a hemodynamic assessment model according to some embodiments of the present disclosure;

DETAILED DESCRIPTION

In order to more clearly illustrate the technical solutions related to the embodiments of the present disclosure, a brief introduction of the drawings referred to the description of the embodiments is provided below. Obviously, drawings described below are only some examples or embodiments of the present disclosure. Those skilled in the art, without further creative efforts, may apply the present disclosure to other similar scenarios according to these drawings.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that the system implements according to the embodiment of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

Figure 1:
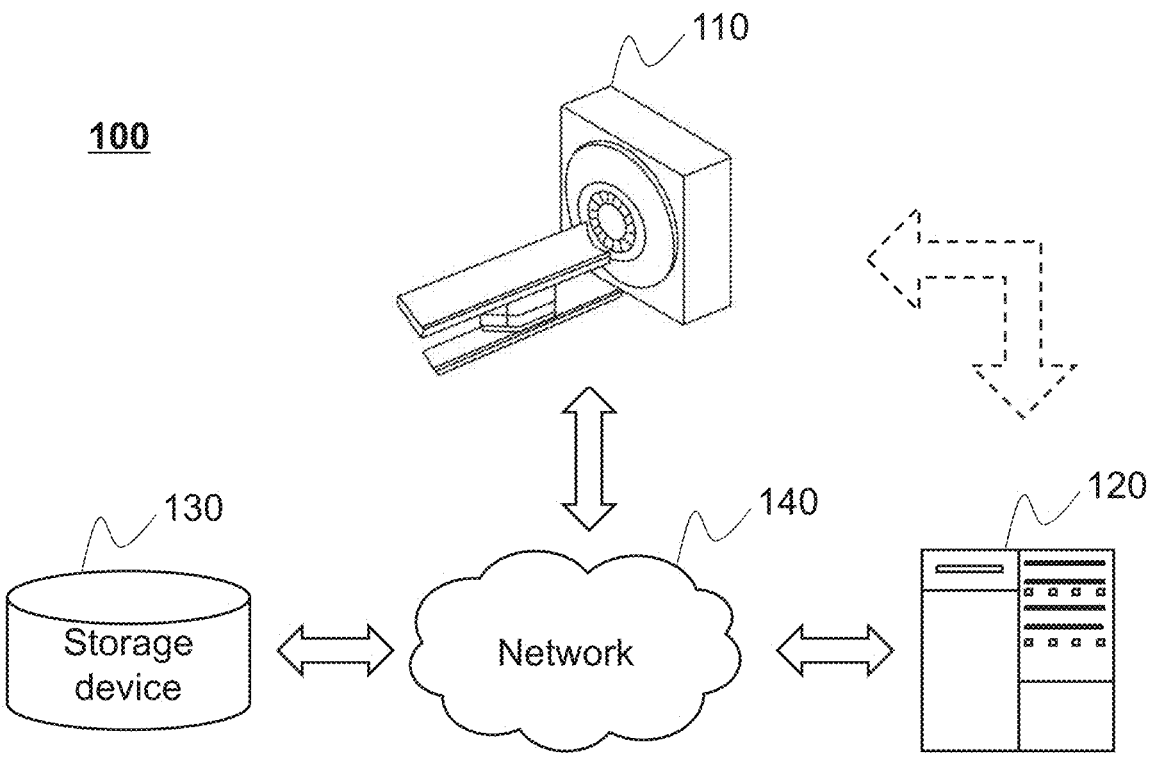
FIG. 1 is a schematic diagram illustrating an exemplary application scenario of a system for determining a hemodynamic parameter according to some embodiments of the present disclosure.

FIG. 1 is a schematic diagram illustrating an exemplary application scenario of a system for determining a hemodynamic parameter according to some embodiments of the present disclosure.

As shown in FIG. 1, the system 100 (hereinafter referred to as the hemodynamic parameter determination system 100) for determining a hemodynamic parameter (e.g., a hemodynamic parameter of the blood flow in a coronary artery) may include an imaging device 110, a processing device 120, a storage device 130, and a network 140.

The imaging device 110 may obtain scan data of a subject by scanning the subject in a detection area or a scanning region. In some embodiments, the imaging device 110 may obtain image data by scanning the subject. In some embodiments, the subject may include a biological subject and/or a non-biological subject. For example, the subjects may include a patient, a man-made object, etc. In some embodiments, the subject may include a specific portion of a body, such as the chest. In some embodiments, the subject may include a specific organ, such as the heart, the esophagus, the trachea, the bronchus, or the like, or any combination thereof.

In some embodiments, the imaging device 110 may be a single modality imaging device, such as an ultrasound diagnostic instrument, a magnetic resonance imaging (MRI) scanner, a computed tomography (CT) scanner, an X-ray imaging device, a positron emission computed tomography (PECT) scanner, a single-photon emission computed tomography (SPECT) imaging device, a magnetic resonance imaging (MRI) scanner, a digital subtraction angiography (DSA) scanner, etc. In some embodiments, the imaging device 110 may be a multimodal imaging device, such as an X-ray-MRI) scanner, a DSA-MRI scanner, a CT-MRI scanner, a CT-PET scanner, or the like, or any combination thereof. The descriptions regarding the imaging devices are merely provided for the purpose of illustration and are not intended to limit the scope of the present disclosure.

In some embodiments, the processing device 120 and the storage device 130 may be a portion of the imaging device 110. In some embodiments, the imaging device 110 may send the image data of the subject to the processing device 120 and the storage device 130 via the network 140 for further processing.

The processing device 120 may process data and/or information obtained and/or extracted from the imaging device 110, the storage device 130, and/or other storage devices. In some embodiments, the processing device 120 may obtain the image data of the subject and obtain a trained machine learning model. Further, the processing device 120 may determine, based on the trained machine learning model, at least one target hemodynamic parameter of the subject.

In some embodiments, the processing device 120 may be a single server or a server group. The server group may be centralized or distributed. In some embodiments, the processing device 120 may be local or remote. For example, the processing device 120 may access information and/or data stored in the imaging device 110 and/or the storage device 130 via the network 140. As another example, the processing device 120 may be directly connected to the imaging device 110 and/or the storage device 130 to access the information and/or data stored therein. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the processing device 120 may be implemented on a computing device. The computing device may be a computer connected to the imaging device 110, such as a laptop or a desktop computer placed in a scanning room or an operation room. In some embodiments, the imaging device 110 and/or other possible system components may include the processing device 120. For example, the processing device 120 or a module that implements a function of the processing device 120 may be integrated in the imaging device 110 and/or other possible system components.

The storage device 130 may be used to store data, instructions, and/or any other information. In some embodiments, the storage device 130 may store data obtained from the imaging device 110 and/or the processing device 120. For example, the storage device 130 may store the image data, the trained machine learning model, relevant data thereof, etc. In some embodiments, the storage device 130 may store data and/or instructions that the processing device 120 uses to execute or uses to perform exemplary methods described in the present disclosure.

In some embodiments, the storage device 130 may include a random access memory (RAM), a read-only memory (ROM), a mass storage, a removable storage, a volatile read-write memory, or the like, or any combination thereof. In some embodiments, the storage device 130 may be implemented on a cloud platform. In some embodiments, the storage device 130 may be connected to the network 140 to communicate with one or more components (e.g., the imaging device 110 or the processing device 120) of the assessment system 100. The one or more components of the assessment system 100 may access data or instructions stored in the storage device 130 via the network 140. In some embodiments, the storage device 130 may be a portion of the processing device 120.

The network 140 may include any suitable network that may facilitate exchange of information and/or data of the assessment system 100. In some embodiments, one or more components (e.g., the imaging device 110, the processing device 120, or the storage device 130) of the assessment system 100 may be connected and/or in communication with other components of the assessment system 100 via the network 140.

In some embodiments, the network 140 may include a wired network, a wireless network, or any combination thereof. For example, the network 140 may include a cable network, an optical network, a telecommunication network, the Internet, a local area network (LAN), a wide area network (WAN), a wireless local area network (WLAN), a metropolitan area network (MAN), a public switched telephone network (PSTN), a Bluetooth network, a ZigBee network (ZigBee), a near-field communication (NFC), an in-device bus, an in-device line, a cable connection, or the like, or any combination thereof. The network connection between the components may be in one more of the ways. In some embodiments, the network 140 may include one or more network access points. For example, the network 140 may include wired or wireless network access points through which one or more components of the assessment system 100 may be connected to the network 140 to exchange data and/or information.

It should be noted that the above description of the application scenario is merely provided for the purpose of illustration and is not intended to limit the scope of the present disclosure. For those skilled in the art, various changes and modifications may be made under the guidance of the present disclosure.

Figure 2:
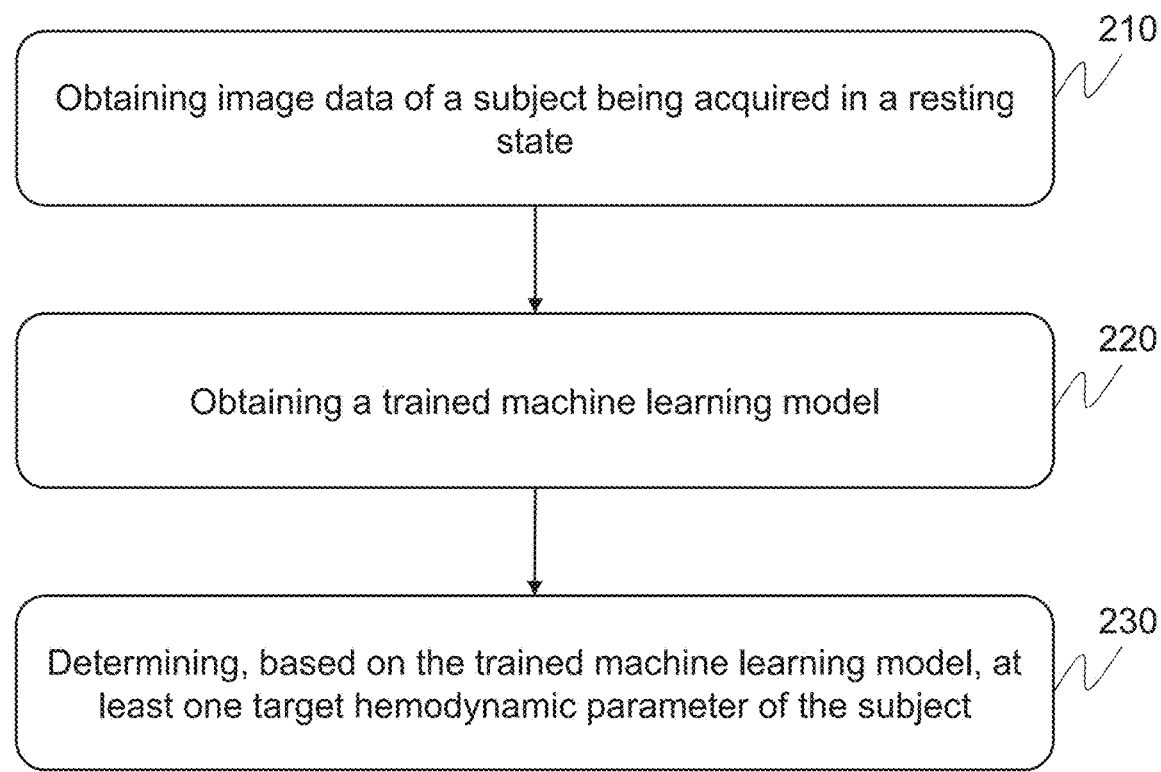
FIG. 2 is a flowchart illustrating an exemplary process for determining a hemodynamic parameter according to some embodiments of the present disclosure.

FIG. 2 is a flowchart illustrating an exemplary process for determining a hemodynamic parameter according to some embodiments of the present disclosure. In some embodiments, the process for determining a hemodynamic parameter may be performed by the processing device 120. For example, the process 200 may be stored in a storage device (e.g., the storage device 130) in the form of a program or an instruction, and the process 200 may be implemented when the processing device 120 executes the program or the instruction. The schematic diagram of the operations of the process 200 presented below is intended to be illustrative. In some embodiments, the process may be accomplished with one or more additional operations not described and/or one or more operations not discussed. In addition, the order in which the operations of the process 200 as illustrated in FIG. 2 and described below is not intended to be limiting. As shown in FIG. 2, the process 200 may include the following operations.

In 210, image data of a subject being acquired in a rest state may be obtained.

The subject may include a blood vessel. For example, the subject may include the coronary artery, the coronary vein, the neck artery, etc.

The image data may be acquired by an imaging device. The imaging device may include a CT scanner, a CT-PET scanner, a CT-MRI scanner, a SPECT, etc. For example, the image data of the subject may be obtained by scanning the subject using the imaging device, such as a dual-source CT device. As a further example, the image data of the coronary artery may be acquired by scanning the coronary artery using the imaging device. More descriptions for the imaging device may be found elsewhere in the present disclosure (e.g., FIG. 1, and the descriptions thereof).

In some embodiments, the image data may include one or more images. For example, the image data may include an image sequence. In some embodiments, the one or more images of the subject may be acquired by the imaging device using a CT angiography technique. In other words, the image data including one or more CTA images. In some embodiments, the image data may be acquired during a time period. The time period may include multiple time phases. Each of the one or more images may be acquired during one of the multiple time phases.

As used herein, the rest rate refers to that the subject remains stationary or substantially stationary and without additional actions or inducement during the scanning of the subject performed by the imaging device to acquire the image data. The image data (e.g., the CTA image) in the rest state may be acquired by the imaging device scanning the subject when the subject (e.g., a patient) is in the rest state (e.g., an ischemic state). For example, the CTA image in the rest state may be acquired by scanning the coronary artery of the subject (e.g., patient) when the subject (e.g., patient) is in the rest state.

In some embodiments, the image data may be obtained by the processing device from the imaging device, the storage device, etc.

In 220, a trained machine learning model (also referred to as a first trained machine learning model) may be obtained.

In some embodiments, the trained machine learning model may be configured to determine one or more hemodynamic parameters of the subject (e.g., coronary artery). The output of the trained machine learning model may include the one or mor hemodynamic parameters of the subject (e.g., coronary artery). The trained machine learning model may also be referred to a hemodynamic parameter assessment model. In some embodiments, the trained machine learning model may be configured to assess a state of the subject (e.g., coronary artery). For example, the trained machine learning model may assess an ischemic state of the heart based on the image data. The output of the trained machine learning model may include the degree of the ischemic state of the subject. In some embodiments, the output of the trained machine learning model may include a report to assess a state of the subject, the report may include one or more hemodynamic parameters of the subject, the ischemic state of the heart, the degree of ischemic state of the subject, or the like, or a combination thereof. The report may be sent to the user terminal for display.

A hemodynamic parameter may be capable of reflecting a feature of blood flow in a blood vessel. In some embodiments, the hemodynamic parameter may include a fractional flow reserve (FFR), a pressure field, a blood flow field, or the like, or a combination thereof. The FFR may be used to assess a lesion of the coronary artery and may also be used to assess the impact of stenosis caused by the lesion of the coronary artery on downstream blood supply.

In some embodiments, the trained machine learning model may include a deep learning network model (e.g., a recurrent neural network (RNN) model, a deep neural network (DNN) model, a convolutional neural network (CNN) model, etc.), a graph neural network (GNN) model, (e.g., a transformer), or the like, or any combination thereof. For example, the trained machine learning model may include a plurality of CNNs and a RNN, where different CNNs are used to process different image data, and the outputs of the different CNNs are input into the RNN, which outputs a prediction result (e.g., the one or mor hemodynamic parameters of the subject) of the trained machine learning model. In some embodiments, the trained machine learning model may include a graph neural network (GNN) model or a transformer network, etc.

In some embodiments, an input of the trained machine learning model may be the image data of the subject and an output of the trained machine learning model may be at least one hemodynamic parameter of the subject. For example, the input of the machine learning model may be the image data of the coronary artery, and the output of the machine learning model may be the at least one hemodynamic parameter of the coronary artery.

As a further example, the input of the trained machine learning model may include the one or more CTA images in the rest state.

In some embodiments, the input of the machine learning model may include a result for a computational fluid dynamics (CFD) simulation based on the image data of the subject. The result of the CFD simulation (also referred as CFD result) may include one or more hemodynamic parameters of the subject, such as the pressure, the flow velocity, etc., of the subject. The processing device may determine the CFD result of the subject based on the image data of the subject by determining a three-dimensional (3D) model of the subject based on the image data of the subject, determining one or more boundary conditions of the subject, and determining, based on the one or more boundary conditions of the subject and the 3D model of the subject, the CFD result of the subject.

In some embodiments, the input of the machine learning model may include the 3D model of the subject and the one or more boundary conditions of the subject.

In some embodiments, the input of the machine learning model may include the image data of the subject and the one or more boundary conditions of the subject.

In some embodiments, the input of the machine learning model may include the image data of the subject, the 3D model of the subject, and the one or more boundary conditions of the subject.

In some embodiments, the input of the machine learning model may include the image data of the subject and the CFD result of the subject.

In some embodiments, the trained machine learning model may be obtained based on multiple sets of sample image data.

In some embodiments, each set of the multiple sets of sample image data may include a first image data and at least one of a second image data or a third image data.

The first image data may be acquired in the rest state of a first sample subject. The first sample subject may be the same as or different from the subject. The first sample subject may include the coronary artery, the neck artery, etc. For example, the first image data may include a CTA image (also referred to as a first CTA image) in the rest state of the first sample subject.

The second image data may be acquired in a hyperemic state of the first sample subject. As used herein, the hyperemic state of an object (e.g., the first sample subject, the subject, the second sample subject) refers to that the object remains motion under an additional load (e.g., action or inducement). In some embodiments, the additional load may be realized via drug injection and the motion of the subject is also referred to as a simulation motion under the drug. The second image data may include a CTA image (also referred to as a second CTA image) in the hyperemic state of the first sample subject.

The third image data may be acquired by scanning a second sample subject associated with the first subject. In some embodiments, the second sample subject may be in flow communication with the first sample subject. For example, the second sample subject may include at least a portion of the myocardium and the first sample subject may include the coronary artery. As a further example, the third image data may include a CTP image of the second sample subject. The CTP image may include a static CTP image and/or a dynamic CTP image. In some embodiments, the third image data may be acquired in the hyperemic state of the second sample subject.

Training samples of the training machine learning model may be constructed based on the multiple set of sample image data. The trained machine learning model may be trained based on the training samples. In some embodiments, each of the multiple training samples may include a CFD result. In some embodiments, each of the multiple training samples may include a reference hemodynamic parameter corresponding to the CFD result. The reference hemodynamic parameters included in the multiple training samples may be data label of the training samples.

In some embodiments, the training samples may include multiple groups. Each group of the multiple groups of the training samples may be determined based on one set of the multiple sets of sample image data. One group of the multiple training samples may include a first sample and at least one of a second sample, a third sample, or a fourth sample.

The first sample may be determined based on the first image data (e.g., the first CTA image in the rest state) of a first sample subject in a set of sample image data. In some embodiments, the first sample may include a first CFD result determined based on the first image data in the set of sample image data. In some embodiments, the first sample may include the first image data in the set of sample image data. In some embodiments, the first sample may include the first image data in the set of sample image data, the 3D model of the first sample subject determined based on the first image data, and one or more first boundary conditions of the first sample subject in the rest state. In some embodiments, the first sample may be obtained according to operations including determining, based on the first image data, a first 3D model representing the first sample subject; determining, based on the first image data, one or more first boundary conditions of the first sample subject, and determining, based on the one or more first boundary conditions and the first 3D model, the first CFD result. More descriptions regarding the first sample may be found in FIG. 4 and the relevant descriptions thereof.

The second sample may be determined based on the second image data (e.g., the second CTA image in the hyperemic state) of the first sample subject in the set of sample image data. In some embodiments, the second sample may include a second CFD result determined based on the second image data in the set of sample image data. In some embodiments, the second sample may include the second image data in one set of the multiple sets of sample image data. In some embodiments, the second sample may include the second image data in the set of sample image data, the 3D model of the first sample subject, and one or more second boundary conditions of the first sample subject in the hyperemic state. In some embodiments, the second sample may be obtained according to operations including determining, based on the second image data, a second 3D model representing the first sample subject, determining, based on the second image data, one or more second boundary conditions of the first sample subject, and determining, based on the one or more second boundary conditions, the second CFD result. In some embodiments, the second image data may be registered with the first image data to obtain a deformation field, and the second CFD result in the hyperemic state may be registered to the first CFD result in the rest state based on the deformation field. More descriptions regarding the second sample may be found in FIG. 4 and the relevant descriptions thereof.

The third sample may be determined based on the first image data (e.g., the first CTA image in the rest state) and the third image data in the set of sample image data. In some embodiments, the third sample may include a third CFD result determined based on the on the first image data (e.g., the first CTA image in the rest state) and the third image data (e.g., the CTP image of the second sample subject). In some embodiments, the third sample may include the first image data (e.g., the CTA image in the rest state) and the third image data. In some embodiments, the third sample may include the first image data (e.g., the first CTA image in the rest state), the third image data, the first 3D model of the first sample subject, and one or more third boundary conditions of the first sample subject determined based on the third image data. In some embodiments, the third sample may be obtained according to operations including determining, based on the first image data, the first 3D model representing the first sample subject; determining, based on the third image data, one or more third boundary conditions of the first sample subject; and determining, based on the one or more third boundary conditions and the first 3D model, the third CFD result. More descriptions regarding the third sample may be found in FIG. 4 and the relevant descriptions thereof.

The fourth sample may be determined based on the second image data (e.g., the CTA image in the hyperemic state) and the third image data in the set of sample image data. In some embodiments, the fourth sample may include a fourth CFD result determined based on the second image data (e.g., the second CTA image in the hyperemic state) and the third image data. In some embodiments, the fourth sample may include the second image data (e.g., the second CTA image in the hyperemic state) and the third image data. In some embodiments, the fourth sample may include the second image data (e.g., the second CTA image in the hyperemic state), the third image data, the second 3D model of the first sample subject, and one or more third boundary conditions of the first sample subject determined based on the third image data. In some embodiments, the fourth sample may be obtained according to operations including determining, based on the second image data, the second 3D model representing the first sample subject; determining, based on the third image data, one or more third boundary conditions of the first sample subject; and determining, based on the one or more third boundary conditions and the second 3D model, the fourth CFD result. In some embodiments, the second image data may be registered with the first image data to obtain the deformation field, and the fourth CFD result in the hyperemic state may be registered to the first CFD result or the third CFD result in the rest state based on the deformation field. More descriptions regarding the second sample may be found in FIG. 4 and the relevant descriptions thereof.

Each of the training samples may serve as an input in the training of the trained learning model. In some embodiments, each of at least a portion of the training sample may correspond to the reference hemodynamic parameter (also referred to as actual hemodynamic parameter). The reference hemodynamic parameter may serve as a desired output in the training of the trained learning model. The reference hemodynamic parameter may also be referred as label of the set of the multiple sets of sample image data.

In some embodiments, the reference hemodynamic parameter may include a FFR. The FFR may be measured by a pressure guidewire technique.

In some embodiments, the trained machine learning model may be obtained by training an initial machine learning model based on the multiple training samples.

In some embodiments, the processing device may obtain the trained machine learning model through supervised training by inputting the CFD results (e.g., the first CFD result, the second CFD result, the third CFDS result) of the multiple training samples and the reference hemodynamic parameters (i.e., the labels) corresponding to the CFD results into the initial machine learning model.

In some embodiments, in the training samples, the count of first samples may exceed a count of second samples, a count of third sample, and/or a count of fourth samples. In some embodiments, a ratio of the count of first samples to the total count of the training samples may exceed a threshold, e.g., 50%, 60%, etc. In some embodiments, a ratio of the total count of second samples and fourth samples to the total count of the training samples may exceed a threshold, e.g., 50%, 60%, etc.

In some embodiments, in a training process, a processing device that is same as or different from the processing device 120 may obtain the multiple sets of sample image data and the reference hemodynamic parameters corresponding to the multiple sets of sample image data, input the multiple sets of sample image data with the labels into an initial machine learning model, construct a loss function through the labels and predicted outputs (i.e., predicted reference hemodynamic parameters) of the initial machine learning model, and iteratively update parameters of the initial machine learning model based on the loss function. When a termination condition is satisfied, the training process may be completed, and the trained machine learning model may be obtained. The termination condition may be that the loss function converges, a count of iterations reaches a threshold, etc.

According to some embodiments of the present disclosure, the trained machine learning model for determining the hemodynamic parameter may be determined using different training samples that are determined based on the CTA image in the rest state, the CTA image in the hyperemic state, and the CTP image. The vascular morphology in two states may be obtained through coronary artery modeling based on the CTA images scanned in the rest state (ischemic state) and the hyperemic state (congested state). As the hemodynamic parameter under the hyperemic state is more significant and accurate for vascular health assessment, a so that the hyperemic state of the coronary artery may be more accurately obtained than the manner that relies merely on a CTA image scanned in a single rest state.

The CFD results that are determined based on the CTA image in the rest state, the CTA image in the hyperemic state, and the CTP may be used as the input of the training of the trained machine learning model, which may make the trained machine learning model obtain more comprehensive information, improving the accuracy of the hemodynamic parameter determined based on the trained machine learning model and the hemodynamic parameter is more significant and accurate for vascular health assessment. The FFR measured by the clinical pressure guidewire may be introduced as the training label during the model training phase, which may make the trained machine learning model determines the hemodynamic parameter such as the FFR more accurately.

In 230, based on the trained machine learning model, at least one target hemodynamic parameter of the subject may be determined.

Figure 3A:
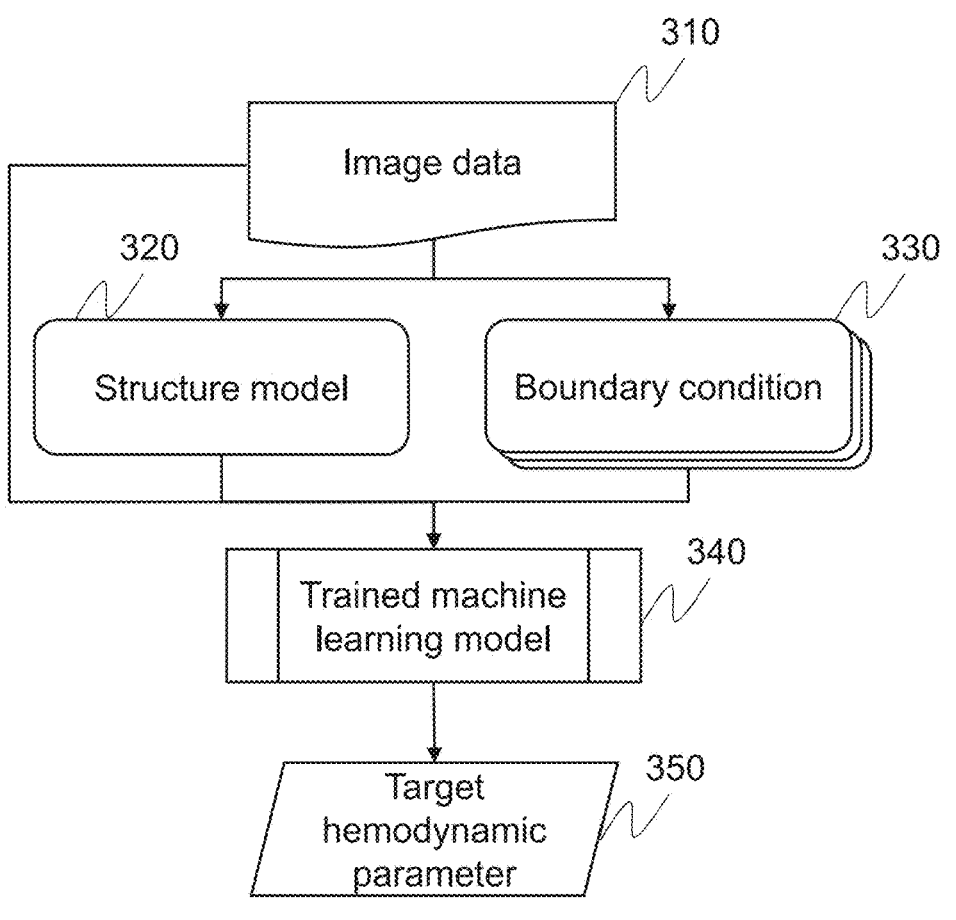
FIG. 3A is an exemplary schematic diagram illustrating determining a target hemodynamic parameter according to some embodiments of the present disclosure.

As shown in FIG. 3A, in some embodiments, the processing device may determine, based on the image data 310 of the subject, a structure model 320 (also referred to as a 3D model) of the subject; determine at least one boundary condition 330 associated with the subject; and determine the at least one target hemodynamic parameter 350 of the subject by inputting the image data 310, the structure model 320, and the at least one boundary condition 330 into the trained machine learning model 340. In some embodiments, the processing device may determine the at least one target hemodynamic parameter 350 of the subject by inputting the structure model 320, and the at least one boundary condition 330 into the trained machine learning model 340.

The structure model may reflect morphological data of the subject such as the shape and the structure of the subject.

In some embodiments, the processing device may determine, based on the image data of the object, the structure model of the subject. For example, the processing device may obtain the structure model of the subject (e.g., the coronary artery) by segmenting the subject (e.g., the coronary artery) in the image data. In some embodiments, the structure model of the subject may be determined by using a segmentation algorithm. Exemplary segmentation algorithms may include a threshold segmentation algorithm, a region growth algorithm, an edge detection algorithm, etc. In some embodiments, the processing device may obtain the structure model of the subject by processing the image data of the subject through a trained machine learning model (also referred to as a second trained machine learning model or an image segmentation model). In some embodiments, the second trained machine learning model may be constructed based on a deep learning network model (e.g., a recurrent neural network (RNN) model, a deep neural network (DNN) model, a convolutional neural network (CNN) model, etc.), a graph neural network (GNN) model, (e.g., a transformer), or the like, or any combination thereof. In some embodiments, the second trained machine learning model may be trained based on multiple training samples (also referred to as second training samples). In some embodiments, each of the second training samples may include a reference structure model of a sample subject and a sample image of the sample subject. The reference structure model may serve as a reference output of the training of the second trained machine learning model and the sample image may serve as an input of the training of the second trained machine learning model. The training of the second trained machine learning model may the same as or similar to the training of the first trained machine learning model. In some embodiments, the second trained machine learning model may be integrated in the first trained machine learning model. The second trained machine learning model and the first training machine learning model in the integrated model may be trained jointly.

A boundary condition refers to a parameter related to flow at an inlet and outlet of the subject. The inlet and outlet of the subject refers to an inlet and outlet for exchange of substance between the subject and other positions. For example, when the subject is the coronary artery, the inlet and outlet of the coronary artery may be a position of the blood vessel in the coronary artery where blood enters the myocardium and a position of the blood vessel in the coronary artery that receives the blood output from the myocardium. The boundary condition of the coronary artery may include an input flow and an output flow of each of at least a portion of branches of the coronary artery, a total input flow and a total output flow of the coronary artery, etc.

More descriptions for determining the boundary condition may be found elsewhere in the present disclosure. See, FIG. 4, FIG. 5, and the relevant descriptions thereof.

In some embodiments, the processing device may determine the at least one target hemodynamic parameter of the subject by inputting the image data, the structure model, and the at least one boundary condition of the subject into the trained machine learning model.

For example, the processing device may determine the at least one target hemodynamic parameter of the subject by inputting the CTA image in the rest state in the image data, the structure model, the boundary condition of the subject into the trained machine learning model.

In some embodiments, the processing device may determine the at least one target hemodynamic parameter of the subject by inputting the CTA image in the rest state, the CTA image in the hyperemic state, the structure model, the boundary condition of the subject into the trained machine learning model. Since the hemodynamic parameter (e.g., FFR) being assessed in the hyperemic state is more meaningful for human health, in the embodiment, the vascular morphology in the two states may be obtained through the coronary artery CTA vascular modeling based on the CTA images scanned in the rest state (ischemic state) and the hyperemic state (hyperemia state), so that the hyperemic state of the coronary artery may be more accurately obtained than the manner that relies merely on the CTA image scanned in the single rest state.

In some embodiments, the processing device may determine the at least one target hemodynamic parameter of the subject by inputting the CTA image in the rest state, the CTP image data, the structure model, and the boundary condition of the subject into the trained machine learning model.

In some embodiments, the processing device may determine the at least one target hemodynamic parameter of the subject by inputting the CTA image in the rest state, the CTA image in the hyperemic state, and the CTP image data into the trained machine learning model.

In some embodiments of the present disclosure, the at least one target hemodynamic parameter of the subject may be determined by inputting the image data, the structure model, and the at least one boundary condition into the trained machine learning model, which may obtain an association relationship between the image data, the structure model, the at least one boundary condition, and the reference hemodynamic parameter by finding the rule from a large amount of historical data using the self-learning ability of the machine learning model, thereby improving the accuracy and efficiency of determining the target hemodynamic parameter.

Figure 3B:
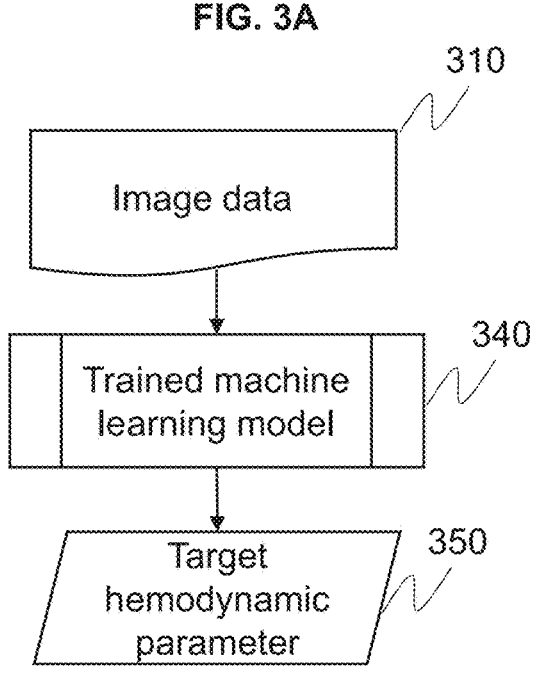
FIG. 3B is another exemplary schematic diagram illustrating determining a target hemodynamic parameter according to some embodiments of the present disclosure.

As shown in FIG. 3B, in some embodiments, the processing device may determine the at least one target hemodynamic parameter 350 of the subject by inputting the image data 310 of the subject into the trained machine learning model 340.

In some embodiments, the processing device may also determine the at least one target hemodynamic parameter of the subject by inputting the CFD result determined based on the image data into the trained machine learning model.

In some embodiments of the present disclosure, the at least one target hemodynamic parameter of the subject may be determined by inputting the image data into the trained machine learning model, which may obtain an association relationship between various input data and the reference hemodynamic parameter by finding the rule from a large amount of historical data using the self-learning capability of the machine learning model, thereby improving the accuracy and efficiency of determining the target hemodynamic parameter.

It should be noted that the description of the process 200 is merely provided for the purpose of illustration, and not intended to limit the scope of application of the present disclosure. For those skilled in the art, various modifications and changes may be made to the process 200 under the guidance of the present disclosure. However, these modifications and changes do not depart from the scope of the present disclosure. For example, the operations 210 and 220 may be synchronized.

Figure 4:
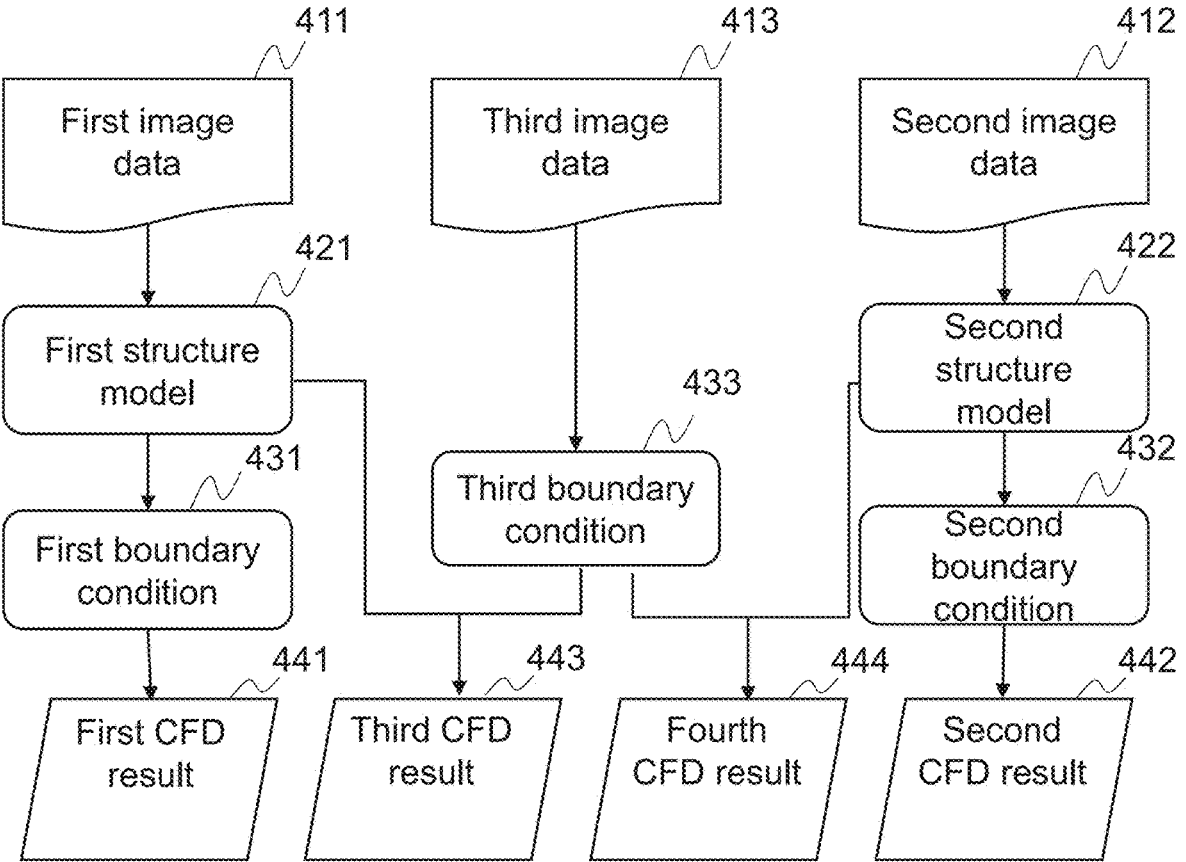
FIG. 4 is an exemplary schematic diagram illustrating determining a computational fluid dynamics (CFD) result according to some embodiments of the present disclosure.

FIG. 4 is an exemplary schematic diagram for determining a CFD result according to some embodiments of the present disclosure.

In some embodiments, the training samples of the trained machine learning model for determining a hemodynamic parameter as described elsewhere in the present disclosure may be obtained according to process as described in FIG. 4. The training samples of the trained machine learning model for determining a hemodynamic parameter may include a first CFD result, and at least one of a second CFD result, a third CFD result, and a fourth CFD result. The first CFD result may be determined based on first image data of a first sample subject in a rest state and the second CFD result may be determined based on second image data of the first sample subject in a hyperemic state. The third CFD result may be determined based on the first image data and third image data of a second sample subject in flow communication with the first sample subject and the fourth CFD result may be determined based on the second image data and the third image data.

In some embodiments, a CFD result of a subject as described elsewhere in the present disclosure may be obtained according to process as described in FIG. 4. For example, the CFD result of the subject in FIG. 3 may be obtained based on the image data of the subject according to process as described in FIG. 4. As a further example, the determination of the CFD result of the subject in FIG. 3 may be similar to or the same as the determination of the first CFD result, the second CFD result, the third CFSD result, or the fourth CFD result.

As shown in FIG. 4, the processing device may determine, based on first image data 411 of a first sample subject, a first structure model 421 of the first sample subject. The first image data 411 may be acquired by an imaging device scanning the first sample subject (e.g., the coronary artery) in the rest state. For example, the first image data 411 may include one or more first CTA images of the first sample subject.

The first structure model (also referred to as a 3D model) refers to a structure model of a subject in the rest state. For example, the first structure model may be a structure model of a coronary artery in the rest state that may reflect morphology of the coronary artery in an ischemic state.

In some embodiments, the processing device may construct, based on the first image data, the first structure model through a first segmentation technique. For example, the processing device may construct the first structure model of the coronary artery by segmenting at least a portion of the coronary artery in the first image data. Exemplary segmentation techniques may include using a threshold segmentation algorithm, a region growing segmentation algorithm, an edge detection segmentation algorithm, or the like, or a combination thereof. In some embodiments, the first segmentation technique may include using a trained machine learning model (also referred to as a first image segmentation model or a second trained machine learning model). The first image segmentation model may be trained based on training samples. Each of the training samples may include a sample image of a sample subject in a rest state. In some embodiments, each of at least a portion of the training samples may be labeled with a label. The label may indicate a segmented sample subject in the sample image. For example, the label may include a mask of the first image data including the segmented sample subject. The label may serve as a reference output of the training of the first image segmentation model. The training of the first image segmentation model may be same as or similar to the training of the trained machine learning model for determining a hemodynamic parameter.

The processing device may determine, a first boundary condition 431 of the first sample subject based on the first image data 411.

In some embodiments, the processing device may determine the first boundary condition based on a corresponding relationship between personalized data of an object and the boundary condition of the object under the rest state. The corresponding relationship between the personalized data (e.g., age, gender, weight, characteristics (e.g., a size, a shape, etc.) of the coronary artery) of the object and the boundary condition of the object may be in form of a table, a function, a model, etc. The corresponding relationship between the personalized data of an object and the boundary condition of the object may include reference boundary conditions of objects in different reference personalized data (e.g., a radial of the outlet of a coronary artery, a radial of the inlet of the coronary artery). The characteristics ((e.g., the radial of the outlet of the first sample subject, the radial of the inlet of the first sample subject) of the first sample subject may be obtained from the first structure model. The processing device may determine the first boundary condition based on the personalized data (of the first sample subject and the corresponding relationship between personalized data of an object and the boundary condition of the object. For example, the processing device may determine a reference size that is same as or similar to the size of the first sample subject, and designate the reference boundary conditions corresponding to the reference size as the first boundary condition of the first sample subject. The corresponding relationship between the personalized data and the boundary condition of the object may be determined based on prior knowledge or historical data.

In some embodiments, the processing device may determine, based on the first structure model and a first table, the first boundary conditions by looking up the first table. In some embodiments, the first table may include correspondences between different reference structure models and different reference boundary conditions in the rest state. In some embodiments, the first table may include correspondences between the different reference structure models, different input flows, and different output flows. The first table may be determined based on priori knowledge or historical data. The processing device may determine one of the reference structure models that has a maximum similarity with the first structure model and designate the reference boundary conditions corresponding to the reference structure as the first boundary conditions.

The processing device may determine, based on the first boundary condition 431 and the first structure model 421, the first CFD result 441. In some embodiments, the processing device may perform meshing based on the first structure model 421 to obtain a first mesh model, solve a hydrodynamic equation (e.g., the Navier Stokes equation) based on the first mesh model and the first boundary condition 431, and determine the first CFD result 441. The processing device may convert the first structure model 421 into a mask and determine the first mesh model by dividing the mask according to a mesh dividing algorithm (e.g., a delauney triangulation algorithm, a person-Strang algorithm, etc.). The processing device may mark boundaries of the first sample subject (e.g., the coronary artery) on the first mesh model. For example, the processing device may mark the inlet, the output, and the wall of each branch of the coronary artery. The processing device may determine the first CFD result 441 by performing an iterative process based on the hydrodynamic equation. For example, the processing device may perform the iterative process according to a semi-implicit method for pressure linked equation (SIMPLE) on the first mesh model. In each iteration, parameters (e.g., pressure, velocity) on each grid of at least a portion of grids of the first mesh model may be updated until the iterative process is terminated. The parameters updated in the last iteration may be designated as the first CFD result.

As shown in FIG. 4, the processing device may determine, based on second image data 412 of the first sample subject, a second structure model 422 of the first sample subject. The second image data 412 may be acquired by an imaging device scanning the first sample subject (e.g., the coronary artery) in the hyperemic state. The second structure model refers to a structure model of a subject in a hyperemic state. For example, the second structure model may be a structure model of a coronary artery in the hyperemic state, which may reflect morphology of the coronary artery in a congested state. In some embodiments, the processing device may construct, based on the second image data, the second structure model through a second segmentation technique. In some embodiments, the second segmentation technique may include using a trained machine learning model (also referred to as a second image segmentation model or a second trained machine learning model). The second image segmentation model may be trained based on training samples. Each of the training samples may include a sample image of a sample subject in a hyperemic state. In some embodiments, each of at least a portion of the training samples may be labeled with a label. The label may indicate a segmented sample subject in the sample image. The label may serve as a reference output of the training of the second image segmentation model. The training of the second image segmentation model may be same as or similar to the training of the trained machine learning model for determining a hemodynamic parameter and/or the training of the first image segmentation model.

In some embodiments, the first segmentation technique may be the same as the second segmentation technique. For example, the first segmentation technique and the second segmentation technique may include using the same image segmentation algorithm. As another example, the first image segmentation model may be the same as the second image segmentation model. In some embodiments, the first segmentation technique may be different from the second segmentation technique. The coronary artery in the CTA image in the hyperemic state may be generally thick due to a scanning factor of the CTA image in the hyperemic state, so the segmentation technique of the CTA image in the hyperemic state may be different from the segmentation technique of the CTA image in the rest state. For example, the first sample subject (e.g., the coronary artery) in the second image data (e.g., a CTA image in the hyperemic state) may be segmented using the second image segmentation model (e.g., a deep learning neural network model (e.g., a vnet neural network model)) and the first sample subject in the first image data (e.g., a CTA image in the rest rate) may be segmented using a region growing segmentation algorithm. In some embodiments of the present disclosure, the CTA in the hyperemic state of the coronary artery may be segmented by segmenting the CTA image in the hyperemic state through the trained machine learning model, which may be conducive to obtaining a more accurate second structure model and avoid adverse effects caused by the scanning factor, etc., of the CTA image in the hyperemic state.

The processing device may determine, based on the image data, at least one second boundary condition 432 of the first sample subject.

In some embodiments, the processing device may determine the second boundary condition based on a corresponding relationship between personalized data of an object and the boundary condition of the object under the hyperemic state. In some embodiments, the processing device may determine the second boundary condition based on a corresponding relationship between a structure model of the object and the boundary condition of the object under the hyperemic state. The determination of the second boundary condition may be the same as or similar to the determination of the first boundary condition.

In some embodiments, the processing device may determine, based on the second boundary condition 432 and the second structure model 422, the second CFD result 442. The determination of the second CFD result 442 may be the same as or similar to the determination of the first CFD result 441. For example, the processing device may perform meshing based on the second boundary condition 432 to obtain a second mesh model, solve the hydrodynamic equation on the second mesh model, and determine the second CFD result 442.

In some embodiments, the processing device may register the second image data 412 with the first image data 411 to obtain a deformation field; and register the second CFD result in the loading result to the first CFD result in the rest state based on the deformation field.

The deformation field refers to a region in which a position of the second image data changes relative to the first image data. The deformation field may present a transformation relationship between spatial positions of corresponding pixel points in the first image data and the second image data. As used herein, the corresponding points in the first image data and the second image data refers to a pixel point in the first image data and a pixel point in the second image data that represent the same portion of a subject represented in the first image data and the second image data.

In some embodiments, the processing device may register the second image data with the first image data to combine corresponding pixel points in the different images to obtain the deformation field. The corresponding pixel points in the different images may represent the same position of the first sample subject in the first image data or the second image data.

In some embodiments, the processing device may determine the second sample by registering the second CFD result to the first CFD result. For example, the processing device may update the second CFD result based on the deformation field In some embodiments of the present disclosure, the deformation field may be obtained by registering CTA image data in a hyperemic state with CTA image data in a rest state, and the CFD results corresponding to the image data may be registered based on the deformation field, which may more quickly determine the one of the second sample and the fourth sample, thereby reducing the amount of calculation.

More descriptions regarding the meshing and the solving the hydrodynamic equation may be found in FIG. 8 and the relevant descriptions thereof.

As shown in FIG. 4, in some embodiments, the processing device may determine, based on the third image data 413, at least one third boundary condition 433 of the first sample subject; and determine, based on the third boundary condition 433 and the first structure model 421, a third CFD result 443.

In some embodiments, the processing device may determine the third boundary condition including the input flow and the output flow of each of at least a portion of branches of the coronary artery, the total input flow and the total output flow of based on the third image data (e.g., a CTP image). For example, the third image data may represent the left ventricular myocardium of the heart. The third image data may include an image sequence including multiple images acquired during different time phases. The processing device may determine a myocardial blood flow (MBF) image of the first sample subject based on the third image data. The MBF image including multiple MBF values each of which corresponds to a voxel of the left ventricular myocardium of the heart. An MBF value may represent the flow of myocardial tissue per 100 ml. The processing device may determine a sum of the multiple MBF values in the MBF image and determine a volume of the left ventricular myocardium of the heart based on the third image data. The processing device may determine a ratio of the sum of the multiple MBF values in the MBF image and the volume of the left ventricular myocardium of the heart as a total input flow (that is same as the total output flow) of the left ventricular myocardium of the heart. The processing device may determine the total input flow (that is same as the total output flow) of the heart based on the total input flow (that is same as the total output flow) of the left ventricular myocardium of the heart that is the $\frac{2}{3}$ of the total input flow (that is same as the total output flow) of the heart. The total input flow (that is same as the total output flow) of the heart may be the total input flow (that is same as the total output flow) of the coronary artery.

In some embodiments, the processing device may determine the input flow and the output flow of each of at least a portion of branches of the coronary artery based on the third image data. For example, the branches of the coronary artery may include a first portion and each branch in the first portion may be in flow communication with a myocardium region of the left ventricular myocardium of the heart. The myocardium region of the left ventricular myocardium of the heart corresponding to a branch in the first portion may supply blood to the branch. The processing device may determine a segmentation result of the first portion of branches and the myocardium region of the left ventricular myocardium of the heart corresponding to each branch in the first portion based on the first image data. The processing device may register the segmentation result with the MBF image to determine the myocardium region of the left ventricular myocardium corresponding to each branch in the first portion in the MBF image. The processing device may determine a sum of MBF values in the myocardium region of the left ventricular myocardium corresponding to each branch in the first portion in the MBF image. The processing device may determine a ratio of the sum of the MBF values in the myocardium region and the volume of the myocardium region as the input flow (or the output flow) of the each branch in the first portion.

In some embodiments, the processing device may determine the input flow and the output flow of each of at least a portion of branches of the coronary artery based the size of the branches of the coronary artery. The processing device may determine a flow distribution ratio of the input flow and the output flow of each branch to the total input flow of the coronary artery according to the radials of output of the branches. For example, the branches of the coronary artery may include a second portion including the remaining branches excepting the first portion of branches. The processing device may determine the input flow and the output flow of each branch in the second portion based on the flow distribution ratio of the input flow and the output flow of each branch to the total input flow of the coronary artery.

For example, the total input flow (also referred to as the input flow) of the coronary artery may be equal to the total output flow of the coronary artery. Therefore, the input flow of each of left and right coronary arteries may need to be equal to a sum of the output flow of each branch of the each of the left and right coronary arteries. It may be assumed that the output flow of each branch is proportional to a third power of the radius of the branch, i.e., $O=aR^3$, where O denotes the outlet flow of each branch, R denotes the cross-sectional radius of the outlet of the branch of the coronary artery, and a is a constant factor. Thus, the flow distribution ratio of the input flow and the output flow of each branch to the total input flow of the coronary artery may be equal to a ratio of the third power of the radius of each branch.

The third image data may include a brightness of a contrast agent in each of the different time phases. The time phases may include a sweeping phase, an arterial phase, a portal vein phase, an equilibrium phase, a delayed phase, etc.

Taking that the second sample subject is the myocardium as an example, the third image data may be the MBF image. In some embodiments, the processing device may register the third image data of the different time phases, determine, based on a change curve of a CT value of each voxel on the myocardium, an MBF value at the voxel, and determine all MBF values of all the voxels to determine the MBF image of the myocardium. The exemplary MBF value of each voxel may be determined according to an Equation (1) as following:

$$MBF = \frac{Maxupslope(TAC)}{Maximum\ (AIF)} \tag{1}$$

where the TAC refers to a time attenuation curve and AIF refers to an arterial input function. In some embodiments, the TAC may be determined based on the third image data (e.g., changes in pixel values during the time phases). In some embodiments, the AIF may be obtained by obtaining a concentration change curve of a contrast medium in an artery during quantitative perfusion.

Figure 6:
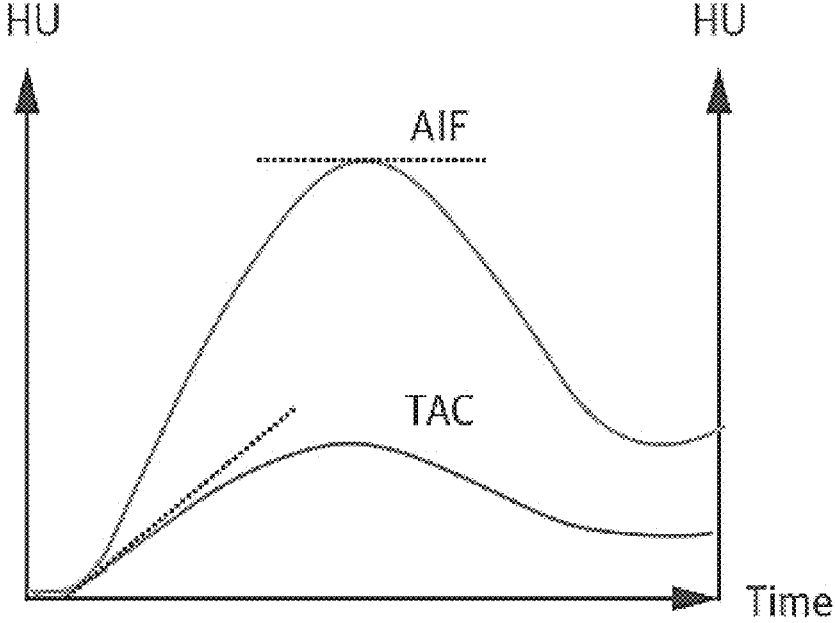
FIG. 6 is a schematic diagram illustrating exemplary time attenuation curves (TAC) and a curve of arterial input function (AIF) of a coronary artery according to some embodiments of the present disclosure.

The Time attenuation curve (TAC) and the Arterial Input Function (AIF) are shown in FIG. 6. It may be seen from FIG. 6 that when the myocardium is ischemic, the slope of the TAC curve is relatively small, and the MBF value is relatively small; and when the myocardium is normal or non-ischemic, the slope of the TAC curve is relatively large, and the MBF value is relatively large, that is, the MBF image may reflect the ischemia of the myocardium.

The determination of the third CFD result 443 may be the same as or similar to the determination of the first CFD result 441. For example, the processing device may perform meshing based on the first structure model 421 to obtain the first mesh model, solve the hydrodynamic equation on the first mesh model based on the third boundary condition 433, and determine the third CFD result 443.

As shown in FIG. 4, in some embodiments, the processing device may determine the fourth CFD result 444 based on the third boundary condition 433 and the second structure model 422. In some embodiments, the third boundary condition 433 used for determining the fourth CFD result 444 may be partially different from the third boundary condition

433 used for determining the third CFD result 443. For example, the branches of the coronary artery may include the second portion including the remaining branches except-ing the first portion of branches. The processing device may determine the input flow and the output flow of each branch in the second portion based on the flow distribution ratio of the input flow and the output flow of each branch to the total input flow of the coronary artery. The processing device may determine the flow distribution ratio of the input flow and the output flow of each branch to the total input flow of the coronary artery according to the radials of output of the branches. For the fourth CFD result 444, the radials of outputs of the branches in the second portion may be determined based on the second structure model 422; and for the third CFD result 443, the radials of outputs of the branches in the second portion may be determined based on the first structure model 421.

The determination of the fourth CFD result 444 may be the same as or similar to the determination of the first CFD result 441. For example, the processing device may perform meshing based on the second structure model 422 to obtain the second mesh model, solve the hydrodynamic equation on the second mesh model based on the third boundary condition 433, and determine the fourth CFD result 444.

Figure 7:
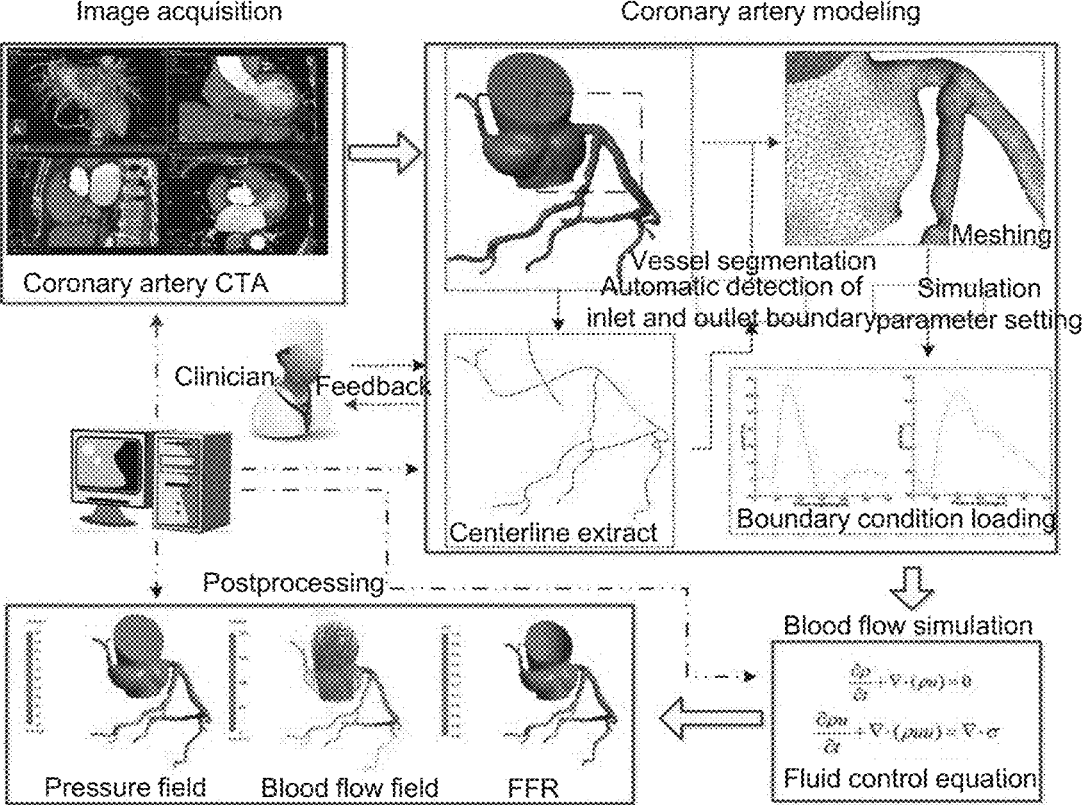
FIG. 7 is a schematic diagram illustrating an exemplary process for computational fluid dynamics (CFD) simulation according to some embodiments of the present disclosure.

More descriptions regarding the meshing and solving the hydrodynamic equation may be found in FIG. 7 and the relevant descriptions thereof. In some embodiments, the processing device may register the second image data 412 with the first image data 411 to obtain a deformation field; and register the fourth CFD result in the loading result to the first CFD result in the rest state based on the deformation field 450.

In some embodiments of the present disclosure, the third boundary condition during the CFD simulation may be evaluated using the CTP image, which may be more accurate and more reflective of real blood flow than a simulation merely using the structure model.

Figure 5:
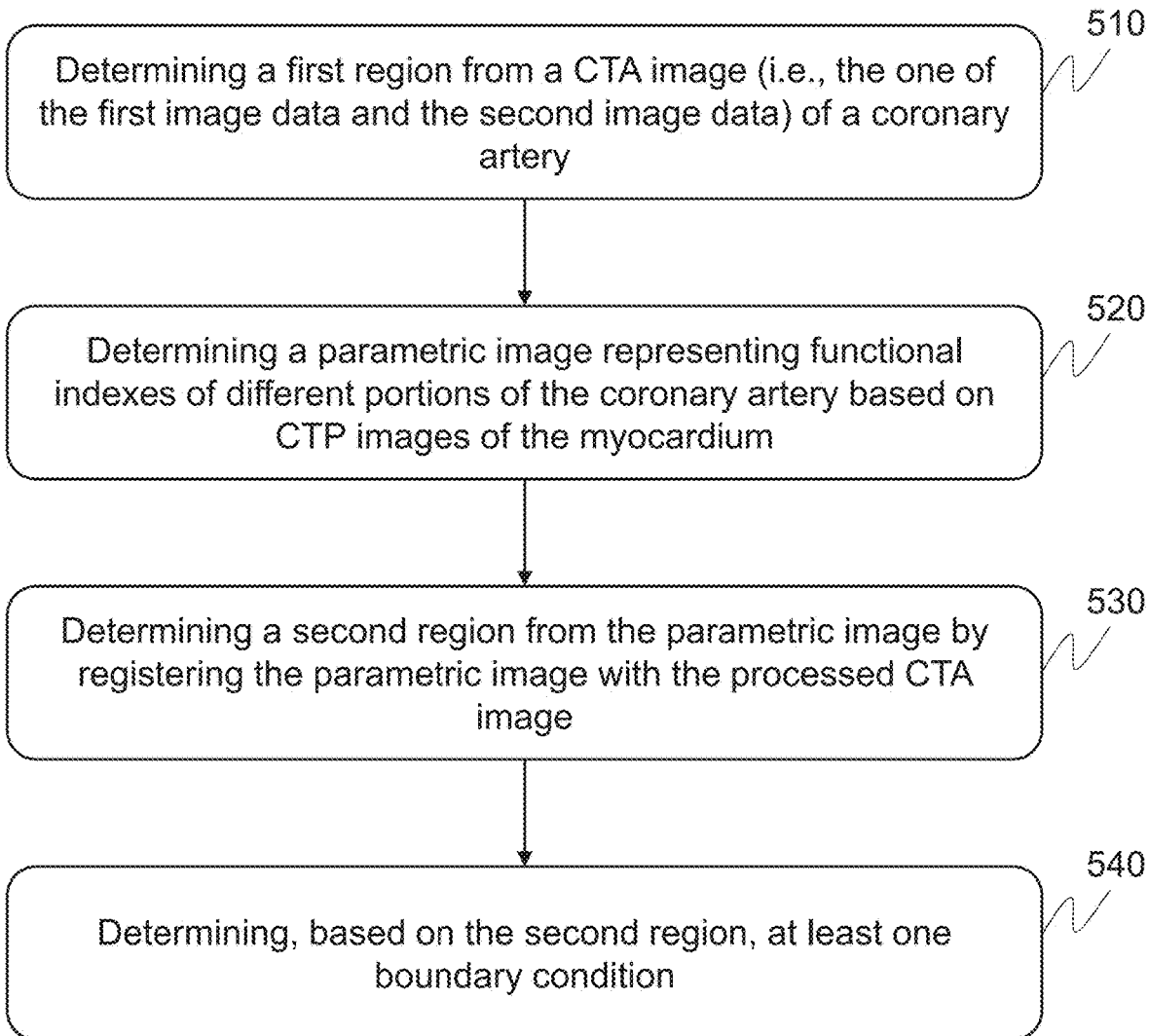
FIG. 5 is a flowchart illustrating an exemplary process for determining at least one third boundary condition according to some embodiments of the present disclosure.

FIG. 5 is a flowchart illustrating an exemplary process for determining at least one third boundary condition according to some embodiments of the present disclosure. For example, the process 500 may be stored in a storage device (e.g., the storage device 130) in the form of a program or an instruction, and the process 500 may be implemented when the processing device 120 executes the program or the instruction. The schematic diagram of the operations of the process 500 presented below is intended to be illustrative. In some embodiments, the process may be accomplished with one or more additional operations not described and/or one or more operations not discussed. In addition, the order in which the operations of the process 500 as illustrated in FIG. 5 and described below is not intended to be limiting. As shown in FIG. 5, the process 500 may include the following operations.

In 510, a first region may be determined from a CTA image (e.g., the first image data or the second image data) of a coronary artery.

The first region may include a myocardium region that supplies blood to each branch of the coronary artery. For example, the first region may include the myocardium region in the CTA image in a rest state (e.g., the first image data or the image data as described in FIG. 3). As another example, the first region may include the myocardium region in the CTA image in a hyperemic state (e.g., the second image data).

In some embodiments, the processing device may deter-mine a segmentation result of the coronary artery and the myocardium by processing the CTA image through an image segmentation technique as described elsewhere in the pres-ent disclosure. The segmentation result may include the CTA image with the segmented the coronary artery and the myocardium. The CTA image with the segmented the coro-nary artery and the myocardium may also be referred to as processed CTA image.

In some embodiments, the processing device may deter-mine the first region by performing a watershed analysis on the processed CTA image. An exemplary watershed analysis technique may include using a nearest neighbor algorithm. For example, the processing device may obtain the myocar-dium region that supplies blood to each branch of the coronary artery by performing the watershed analysis on the processed CTA image using the nearest neighbor algorithm.

In 520, a parametric image representing a functional index of different portions of the coronary artery may be deter-mined based on CTP images of the myocardium.

The functional index refer to an index related to the myocardium, for example, an MBF.

The parametric image refers to an image that reflects changes in the functional index, for example, an MBF image. Taking the myocardium as an example, the process-ing device may determine an MBF value of each voxel representing a portion of the myocardium based on a change curve of a CT value of each portion of the myocardium and obtain the MBF image of the myocardium according to all the MBF values of all the voxels. More descriptions regard-ing determining the MBF image may be found in the related descriptions above.

In 530, a second region may be determined from the parametric image by registering the parametric image with the processed CTA image.

Taking that the first region is the myocardium region as an example, the second region may also referred to be as a blood supply region of each branch of the coronary artery in the parametric image or a myocardium region corresponding to each branch of the coronary artery in the parametric image.

In some embodiments, the processing device may deter-mine the second region from the parametric image by registering the parametric image with the processed CTA image. An exemplary image registration technique may include a feature-based image registration technique, a tem-plate matching image registration technique, etc.

In 540, at least one boundary condition may be deter-mined based on the second region.

In some embodiments, the processing device may deter-mine the boundary condition by accumulating the flow on the second region. For example, the processing device may determine a sum of the MBF values in the blood supply region of each branch The processing device may determine the input flow of each branch of the coronary artery by determining a ratio of the sum of the MBF values in the blood supply region of each branch to the volume of a myocardium portion represented by the blood supply region.

In some embodiments, the at least one boundary condition determined based on the CTA image and the CTP images may be used to determine a CFD result and/or a target hemodynamic parameter according to embodiments as described elsewhere in the present disclosure.

In some embodiments of the present disclosure, the at least one boundary condition may be determined by regis-tering the parametric image in the CTP with the CTA image, so that the corresponding boundary condition may be deter-mined quickly and accurately.

FIG. 7 is a schematic diagram illustrating an exemplary process of CFD simulation according to some embodiments of the present disclosure.

As shown in FIG. 7, in some embodiments, the CFD simulation may include meshing, boundary determination, boundary condition setting, and hydrodynamic equation solving.

In some embodiments, the meshing may convert a structure model of a coronary artery into a mesh model that may be used for CFD simulation. A Delauney meshing technique may be used to dividing the structure model of the coronary artery into the mesh model. The Delauney meshing technique may be used to convert the structure model of the coronary artery into a tetrahedral mesh (i.e., the mesh model), and every triangle on the tetrahedron of the tetrahedral mesh is an acute triangle.

In some embodiments, after the mesh model is determined, the boundary of the coronary artery may be marked on the mesh model, i.e., an inlet, an outlet, and a wall surface of the coronary artery where there is no fluid flow. In some embodiments, the processing device may simulate flow of the coronary artery using a CFD technique. The inlet may be an inlet of the coronary artery, the outlet may be an end of the coronary artery extracted from each branch, a plane of a truncated cross-section of the each branch of the coronary artery may be taken as an outlet of the coronary artery, and other regions may be wall surfaces where there is no fluid flow.

In some embodiments, the processing device may determine at least one boundary condition based on priori knowledge. The at least one boundary condition may include an inlet flow (also referred to as total inlet flow) of the coronary artery, the input flow of each of at least a portion of branches of the coronary artery, the output flow of each of at least a portion of branches of the coronary artery, etc. As described above, the inlet flow (i.e., the total inlet flow) of the coronary artery and the input flow of each of at least a portion of branches of the coronary artery may be estimated based on the CTP images as described elsewhere in the present disclosure (e.g., FIG. 4 and FIG. 5, and the descriptions thereof). After the total inlet flow is determined, for an uncompressed fluid, the inlet flow may be equal to a total outlet flow of the coronary artery. Therefore, the total inlet flow of each of left and right coronary arteries may be equal to a sum of the outlet flow of each branch of the each of left and right coronary arteries. The outlet flow of each branch of a coronary artery may be determined based on a flow distribution between outlets of branches of the coronary artery (e.g., the left coronary artery, the right coronary artery, etc.)

In some embodiments, the processing device may determine the flow distribution (also referred to as the flow distribution ratio) between outlets of branches of the coronary artery according to a radius of each of the outlets of branches of the coronary artery. For example, the processing device may assume that the output flow of each of the branches of the coronary artery is proportional to a third power of the radius of the outlet of a branch of the coronary artery, i.e., $O=aR^3$, where O denotes the outlet flow of each branch of the coronary artery, R denotes the cross-sectional radius of the branch of the coronary artery at the outlet, and "a" is a constant factor. Since the total outlet flow of the branches of the coronary artery is already obtained, only a proportion of radii of the outlets of the branches of the coronary artery may be needed, and a specific value of "a" may not need to be known.

In some embodiments, the processing device may obtain input flow of each branch of at least a portion of branches of the coronary artery based on third image data (e.g., CTP image) as described elsewhere where in the present disclosure (e.g., FIG. 4, FIG. 5, and FIG. 10, and the descriptions thereof).

In some embodiments, solving the hydrodynamic equation may be performed iteratively on the mesh model after the boundary condition is determined. In some embodiments, the Navier-Stokes equation may be solved using a semi-implicit method for pressure linked equation (SIMPLE). A calculation speed of the SIMPLE may be relatively fast since only a portion of parameters on some meshes (also referred to as grids) of the mesh model may be updated at each iteration. After convergence of the iterative process including multiple iterations, the parameter such as pressure and flow on each mesh may tend to be stabilized, and a pressure value on each mesh after solving may be obtained. According to the pressure value on the mesh, an FFR value (i.e., a proportion of the blood pressure on the mesh to a blood pressure at the inlet of the coronary artery) may be obtained. In some embodiments, the processing device may also further determine a target hemodynamic parameter (e.g., FFR) through a CFD result such as pressure or flow.

In some embodiments, the processing device may perform modeling on the first image data and the second image data (e.g., the CTA image in the rest state and the CTA image in the hyperemic state) to obtain two structure models of the subject in the first image data and the second image data, respectively, estimate boundary conditions according to two manners including using a common boundary condition estimation manner and a boundary condition estimation manner based on the third image data, respectively, and obtain four CFD results by performing stimulation based on the two structure models and the boundary conditions determined according the two manners.

Since the CFD simulation has some shortcomings, such as high sensitivity to masks, low fault tolerance for plaque and stenosis identification, or long computation time, the deep learning manner may be used to determine the FFR. The training of the deep neural network model may include obtaining the hemodynamic parameter using the CFD simulation as a result criterion of a training set. After that, the hemodynamic parameter may be determine using the trained neural network. In general, however, there may be no greater advantage in accuracy using the deep neural network model to determine the FFR than using CFD simulation to determine FFR if the deep neural network model is obtained based on training set that merely determined based on the CTA images in the rest state a with the common boundary condition estimation manner.

In some embodiments of the present disclosure, modeling may be performed on the first image data and the second image data (e.g., CTA images in the rest state and the hyperemic state), and the CFD simulation may be performed based on boundary conditions that are determined using the common boundary condition estimation manner and the boundary condition estimation manner based on the third image data. Since the different structure models and boundary condition estimation manners are used, the results of CFD simulations determined under different conditions may be different. Therefore, in order to solve the problem, the deep learning may need to be further applied.

More descriptions regarding the determining the CFD results based on the machine learning model may be found in FIG. 2, FIG. 3A, FIG. 3B, FIG. 4, and the relevant descriptions thereof.

FIG. 8 is a flowchart illustrating an exemplary process for training a hemodynamic assessment model according to some embodiments of the present disclosure. As shown in FIG. 8, in some embodiments, the process 800 for training the hemodynamic assessment model may include operation 810, operation 820, and operation 830.

In 810, first image data and second image data of a subject may be obtained. More descriptions regarding the first image data and the second image data may be found in FIG. 4 and FIG. 10 and the relevant descriptions thereof.

In 820, multimodal CFD results of the subject may be obtained by performing a CFD simulation based on the first image data and the second image data, respectively.

In some embodiments, the multimodal CFD results may include a first CFD result and at least one of a second CFD results, a third CFD result, or a fourth CFD result.

More descriptions regarding the CFD simulation and the CFD results may be found elsewhere in the present disclosure.

In 830, training samples may be obtained based on the multimodal CFD results, and the training samples may be input into a machine learning model for model training.

Figure 9:
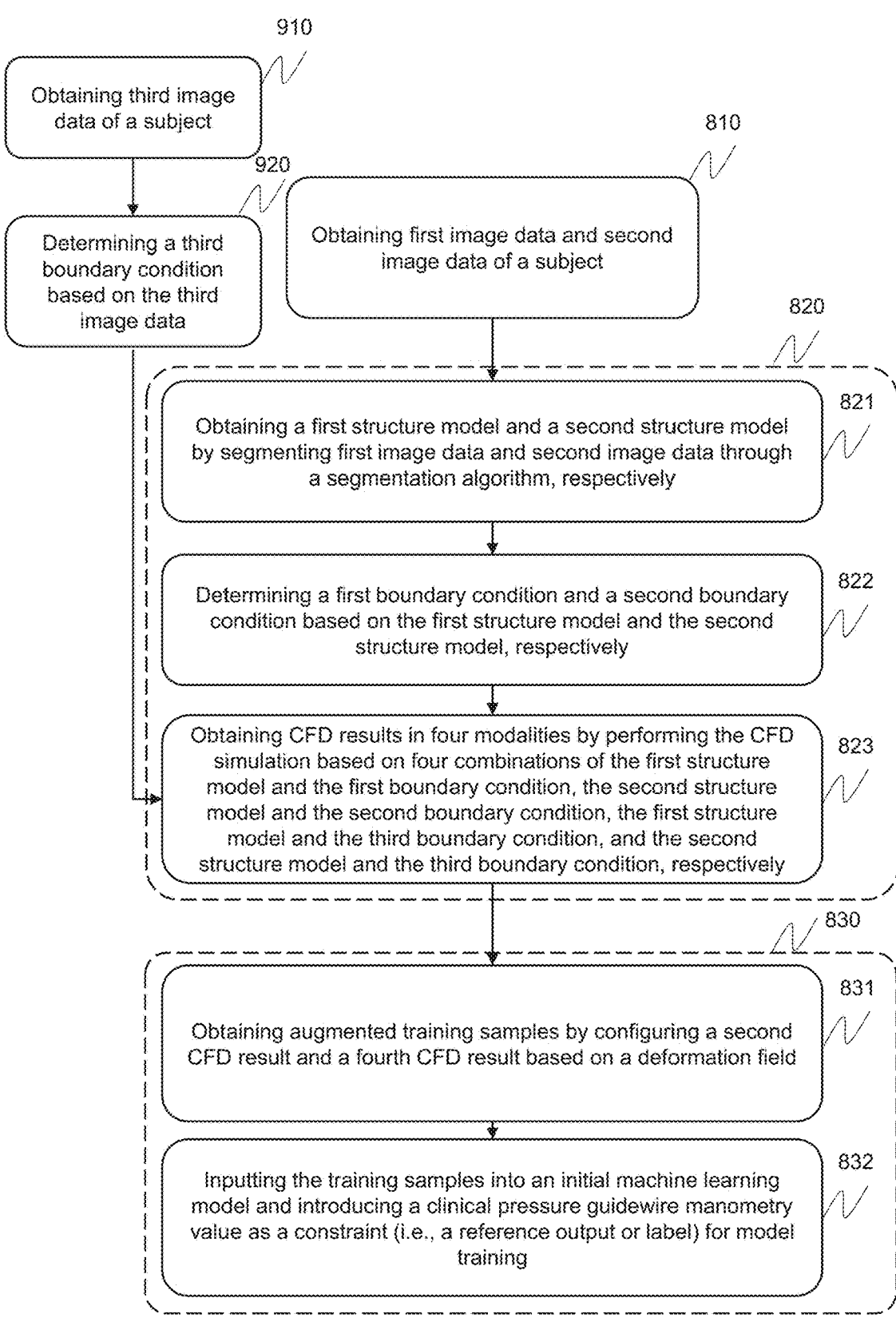
FIG. 9 is a flowchart illustrating another exemplary process for training a hemodynamic assessment model according to some embodiments of the present disclosure.

FIG. 9 is a flowchart illustrating another exemplary process for training a hemodynamic assessment model according to some embodiments shown in the present disclosure.

As shown in FIG. 9, in some embodiments, operations 910 and 920 may be performed.

In 910, third image data of a subject may be obtained.

In 920, a third boundary condition may be determined based on the third image data.

As shown in FIG. 9, in some embodiments, operation 820 may also include the operations 821, 822, and 823.

In 821, a first structure model and a second structure model may be obtained by segmenting first image data and second image data through a segmentation algorithm, respectively.

In some embodiments, performing a CFD simulation based on the first image data may include obtaining the first image data, segmenting a coronary artery in the first image data, and obtaining the first structure model based on the segmented coronary artery. Physiological parameters such as flow of the first structure model may be determined, and a first boundary condition of the CFD simulation may be estimated based on the physiological parameter. Since it is necessary to expand a blood vessel by injecting adenosine to obtain an FFR value in a congested state (hyperemic state) when a pressure of FFR is measured clinically with a pressure guidewire, it may be also necessary to simulate a blood flow state in the congested state in the CFD simulation. In some embodiments, the CTA of the coronary artery and cardiac output flow may be obtained in a rest state, an input flow of the coronary artery in the congestive state may be estimated based on an input flow of the coronary artery in the rest state. For example, the total input flow of the left and right coronary arteries may be estimated based on the cardiac output flow. Generally, the input flow of a coronary artery in the rest flow accounts for 4% of the overall cardiac output flow, and if the cardiac output flow is CO, the total input flow of the coronary artery in the rest state may be CO*4%. Since in the congested state with 140 micrograms of adenosine injection, the input flow of the coronary artery in the congested state is four times of the input flow of the coronary artery in the rest state, the input flow of the coronary artery in the congested state may be CO*4%*4. The above process is an example of estimating boundary conditions in the hyperemic state based on the first image data in the rest state. In fact, scientists have proposed many different mathematical models based on experiments for estimating a relationship between blood flow parameters in the rest and hyperemic states. However, these models have a common disadvantage, that is, these models are all non-individualized models. The approximate relationship between the blood flow parameters in the rest and hyperemic states may be obtained by fitting through a large number of experiments. However, because of great differences between humans and the different types and doses of vasodilators injected during the congestion, a conversion relationship between the blood flow parameters in the rest and hyperemic states obtained by mathematical models may only be estimated. When the blood flow parameters such as the blood flow in the hyperemic state are assessed, a change in the coronary artery vessel may not be taken into account The structure model in the rest state is still used when performing the CFD simulation or other calculations. In fact, in the congested state, a vessel diameter of the coronary artery is expanded, and in particular, the expansion of the coronary artery is not equal proportional. Expansion of the coronary artery in a non-lesional region may be relatively large and expansion of the coronary artery in a stenotic region may be relatively small or no expansion of the coronary artery in the stenotic region. The nonlinear expansion proportion may also result in the fact that the difference between the hyperemic state and the rest state is not only manifested in an increase in the total flow, but also in a lot of localized inhomogeneous information. Therefore, if only the CTA image in the rest state is applied for determining an FFR, an error may be relatively large.

In some embodiments, performing the CFD simulation based on the second image data may include obtaining the second structure model through the segmentation algorithm based on the second image data. The coronary artery in the second image data may be generally thick due to a factor such as scanning of the CTA image in the hyperemic state, so the segmentation manner of the CTA image in the hyperemic state may be different from the segmentation manner of the CTA image in the rest state. The coronary artery of the second image data may be segmented using a deep learning technique. In the manner, the coronary artery in the second image data may need to be manually labeled, a labeled gold standard may be learned using a vnet neural network, and the second structure model at the segmentation may be obtained.

In 822, a first boundary condition and a second boundary condition may be determined based on the first structure model and the second structure model, respectively.

In 823, CFD results in four modalities may be obtained by performing the CFD simulation based on four combinations of the first structure model and the first boundary condition, the second structure model and the second boundary condition, the first structure model and the third boundary condition, and the second structure model and the third boundary condition, respectively.

As shown in FIG. 9, in some embodiments, the operation 830 may also include the operation 831.

In 831, augmented training samples may be obtained by configuring a second CFD result and a fourth CFD result based on a deformation field. The deformation field may be determined based on a registration result of the CTA image in the rest state and the CTA image in the hyperemic state of the coronary artery.

As shown in FIG. 9, in some embodiments, operation 830 may also include operation 832.

In 832, the training samples may be inputted into an initial machine learning model, and a clinical pressure guidewire manometry value may be introduced as a constraint (i.e., a reference output or label) for model training. Specifically, the FFR value measured by the clinical pressure guidewire may be introduced as the constraint on the result during the model training.

After the machine learning model is trained, and when the machine learning model is used, a target hemodynamic parameter may be determined by simply inputting the CTA image in the rest state and the structure model (i.e., the first structure model) built based on the CTA image in the rest state to the trained machine learning model. Since there is already a large amount of information about CTA in the hyperemic state and perfusion information in the network training stage, the hemodynamic parameters determined by the trained machine learning model may be also better simulate a real blood flow situation and obtain more accurate results than those determined by a trained machine learning model that merely relies on the CTA image in the rest state and the common boundary condition estimation manner.

Since the inputs of the embodiment are all values on a three-dimensional image, the trained machine learning model may be structured as a multi-layered convolutional neural network (CNN), and since the obtained results are values of hemodynamic parameters on a centerline of the coronary arteries, the output values may be obtained using a recurrent neural network (RNN) at an output layer, so that the overall processing may be performed using a CNN+RNN manner. As a variation example, the trained machine learning model may also be a graph neural network, a transformer network, etc. The various different networks may differ in the simulation accuracy of the result, but this difference may not affect the implementation of the present disclosure.

In some embodiments of the present disclosure, the vascular morphology in the two states may be obtained by performing modeling of the coronary artery CTA blood vessels based on the CTA images scanned in the two states of the rest state and the hyperemic state. Since the coronary artery blood flow parameter (e.g., FFR) being assessed in the hyperemic state is more meaningful for human health, the hyperemic state of the coronary artery may be more accurately obtained than the manner that relies merely on the CTA image in the single rest state. Determining the output flow during the CFD simulation using a myocardial perfusion CTP image may be more accurate than determining the output flow using merely model simulation. The values obtained from the above more accurate CTA model in the hyperemic state and the myocardial perfusion CTP may be used as inputs of the network, which may make the neural network obtain more comprehensive information. The FFR value obtained by the pressure guidewire manometry may be used as the gold standard for training, which may obtain a more accurate relationship between the CTA images and the FFR of the blood flow parameter.

FIG. 10 is an exemplary schematic diagram illustrating a system for training a hemodynamic assessment model shown according to some embodiments of the present disclosure. As shown in FIG. 10, the system 1000 for training the hemodynamic assessment model of a coronary artery may include an obtaining module 1010, a simulation module 1020, and a training module 1030.

The obtaining module 1010 may be configured to obtain data for training of the hemodynamic assessment model, such as the first image data and second image data of a first subject (also referred to as a first sample subject), and the third image data of a second subject (also referred to as a second sample subject) associated with the first subject.

The simulation module 1020 may be configured to obtain multimodal CFD results of the first subject by performing a CFD simulation based on the first image data and at least one of the second image data and the third image data.

The training module 1030 may be configured to obtain training samples based on the multimodal CFD results and input the training samples into a machine learning model for model training.

Figure 11:
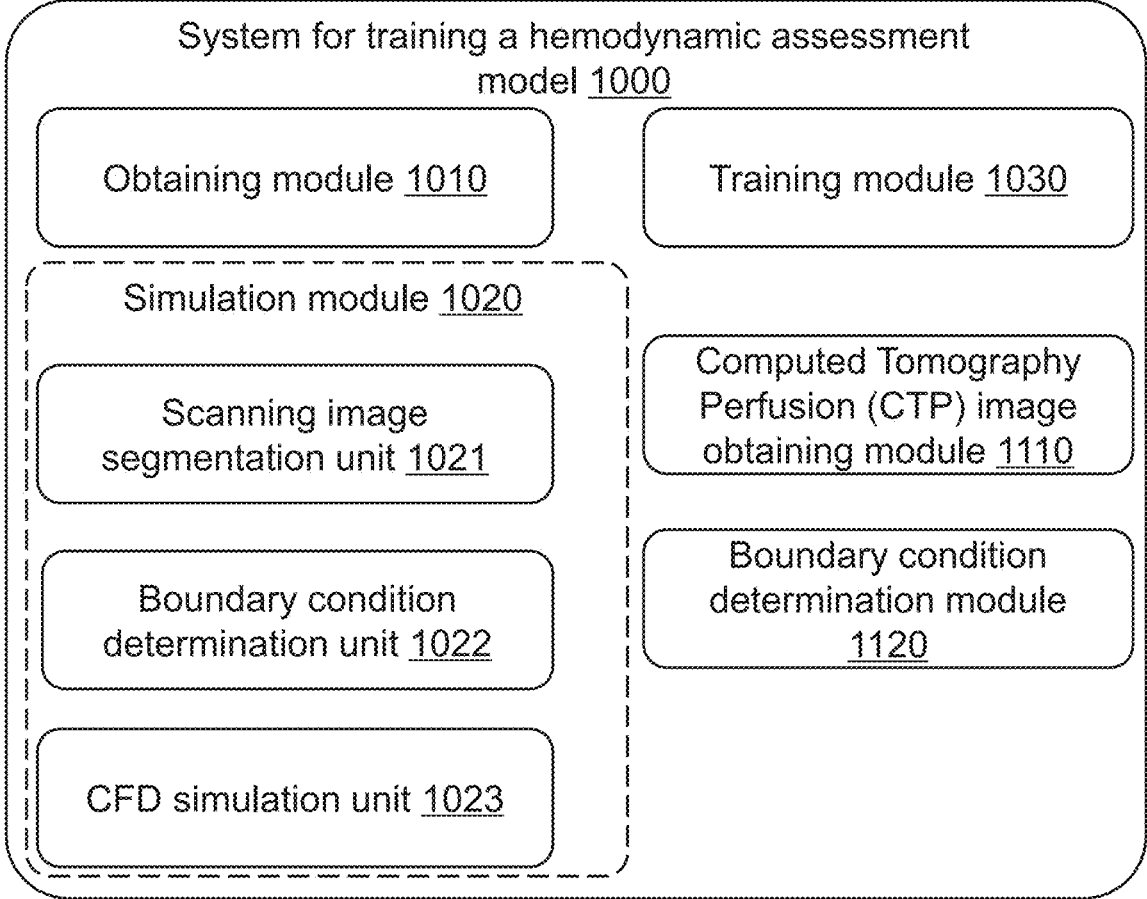
FIG. 11 is another exemplary schematic diagram illustrating a training system for a hemodynamic assessment model according to some embodiments of the present disclosure.

FIG. 11 is another exemplary schematic diagram illustrating a system for training a hemodynamic assessment model according to some embodiments shown in the present disclosure. As shown in FIG. 11, in some embodiments, the system 1000 for training the hemodynamic assessment model may further include a CTP image obtaining module 1110 and a boundary condition determination module 1120.

The CTP image obtaining module 1110 may be configured to obtain third image data of a coronary artery.

The boundary condition determination module 1120 may be configured to determine a third boundary condition based on the third image data.

In some embodiments, the simulation result obtaining module 1020 may also include a scanning image segmentation unit 1021, a boundary condition determination unit 1022, and a CFD simulation unit 1023.

The scanning image segmentation unit 1021 may be configured to obtain a first structure model and a second structure model by segmenting first image data and second image data through a segmentation algorithm, respectively.

The boundary condition determination unit 1022 may be configured to determine a first boundary condition and a second boundary condition based on the first structure model and the second structure model, respectively.

The CFD simulation unit 1023 may be configured to obtain CFD results in four modes by performing a CFD simulation based on four combinations of the first structure model and the first boundary condition, the second structure model and the second boundary condition, the first structure model and the third boundary condition, and the second structure model and the third boundary condition, respectively.

Figure 12:
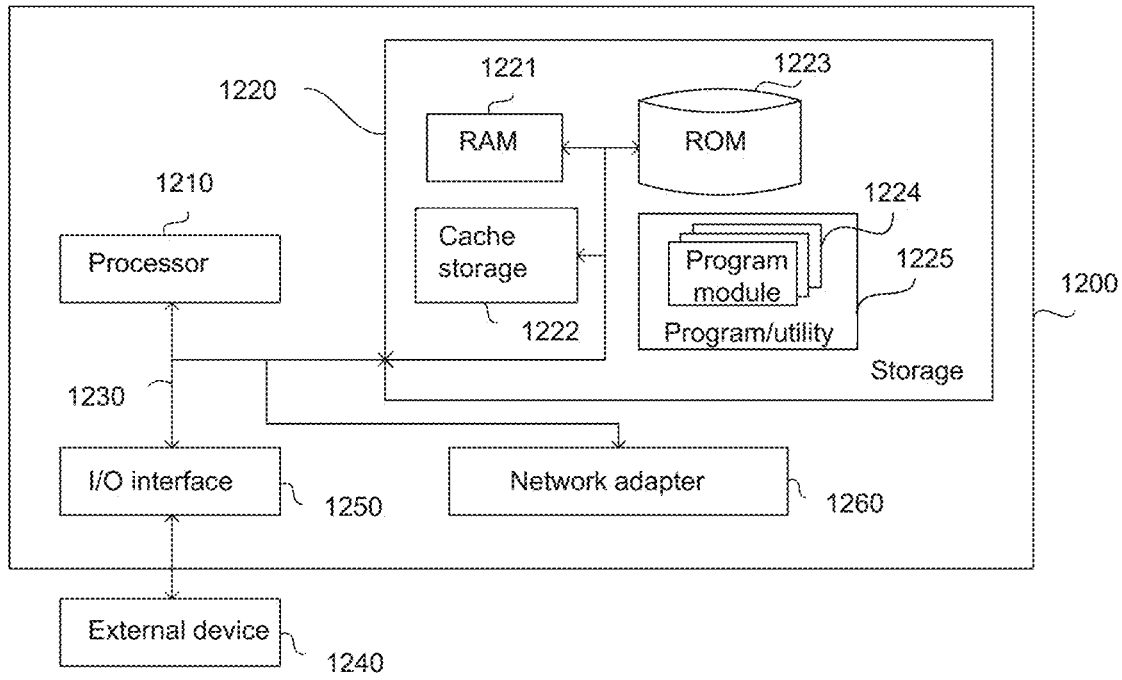
FIG. 12 is a structural diagram illustrating an exemplary electronic device according to some embodiments of the present disclosure.

FIG. 12 is a structural diagram illustrating an exemplary electronic device according to some embodiments of the present disclosure.

As shown in FIG. 12, in some embodiments, the electronic device may include a storage, a processor, and a computer program stored in the storage and operable on the processor. When the processor executes the program, the method for the hemodynamic assessment model of the coronary artery or the method for determining the hemodynamic parameter of the coronary artery may be implemented. The electronic device 1200 shown in FIG. 12 is merely an example and may not impose any limitation on the functionality and scope of use of embodiments of the present disclosure.

As shown in FIG. 12, the electronic device 1200 may be represented in the form of a general-purpose computing device, for example, the electronic device 1200 may be a server device. A component of the electronic device 1200 may include, but is not limited to, at least one processor 1210, at least one storage 1220, a bus 1230 that connects different system components (including the storage 1220 and the processor 1210).

The bus 1230 may include a data bus, an address bus, and a control bus.

The storage 1220 may include a volatile storage, such as a random access memory (RAM) 1221 and/or a cache storage 1222, and may further include a read-only memory (ROM) 1223.

The storage 1220 may also include a program/utility 1225 having a set (at least one) of program modules 1224. The program modules 1224 may include, but are not limited to: an operating system, one or more applications, other program modules, and program data. Each or a certain combination of the examples may include an implementation of a networked environment.

The processor 1221 may perform various functional applications and data processing (e.g., the method for training the hemodynamic assessment model of the coronary artery or the method for determining the hemodynamic parameter of the coronary artery) by running a computer program stored in the cache storage 1222.

The electronic device 1200 may also communicate with one or more external devices 1240 (e.g., a keyboard or a pointing device). The communication may be carried out via an input/output (I/O) interface 1250. The electronic device 1200 may also communicate with one or more networks (e.g., a local area network (LAN), a wide area network (WAN), and/or a public network (e.g., the Internet)) via a network adapter 1260. As shown in FIG. 12, the network adapter 1260 may communicate with other modules of the electronic device 1200 via the bus 1230. It should be understood that, although not shown in the figure, other hardware and/or software modules may be used in conjunction with the electronic device 1200, including, but not limited to: microcode, a device driver, a redundant processor, an external disk drive array, a Redundant Array of Independent Disk (RAID) system, a tape drive, a data backup storage system, etc.

It should be noted that although reference is made to a number of units/modules or sub-units/modules of the electronic device in the detailed description above, the division is merely exemplary and not mandatory. In fact, according to embodiments of the present disclosure, the features and functions of two or more units/modules described above may be materialized in a single unit/module. Instead, the features and functions of the one unit/module described above may be further divided to be materialized by multiple units/modules.

The present embodiment provides a non-transitory computer-readable storage medium including a computer program. When the program is executed by the processor, the training method of the hemodynamic assessment model or the method for determining the hemodynamic parameter may be implemented.

The non-transitory readable storage medium may be employed more specifically. The non-transitory readable storage medium may include, but is not limited to: a portable disk, a hard disk, a random access memory, a read-only memory, an erasable programmable read-only memory, an optical storage device, a magnetic storage device, or any suitable combination thereof.

In possible embodiments, the present disclosure may also be realized in the form of a program product, which may include program code. When the program product is run on a terminal device, the program code is configured to enable the terminal device to execute the method for training the hemodynamic assessment model or the method for determining the hemodynamic parameter.

The program code for executing the present disclosure may be written in any combination of one or more programming languages. The program code may be executed entirely on a user device, partially on a user device, as a separate software package, partially on the user device and partially on a remote device, or completely on the remote device.

The beneficial effects of embodiments of the present disclosure may include, but are not limited to: (1) various information contained in image data in the rest state and the hyperemic state may be taken into account, which is conducive to more accurately determining the target hemodynamic parameter of the subject; (2) the trained machine learning model for determining hemodynamic parameters may learn a large amount of the CTA image data in the hyperemic state and the CTP image data in the training stage, so that the hemodynamic parameter determined by the trained machine learning model is more accurate and can better simulate the real blood flow situation in the hyperemic state; (3) the FFR value may be measured by introducing the clinical pressure guidewire as a kind of constraint on the result in the training stage of the trained machine learning model for determining hemodynamic parameters, so that the trained machine learning model may determine the hemodynamic parameter such as the FFR value with improved accuracy; (4) multimodal CFD simulation results may be obtained; (5) the CTA image in the hyperemic state may be segmented using a trained machine learning model for image segmentation, which is conducive to obtaining a more accurate second structure model, thereby avoid adverse effects caused by the scanning factor of the CTA image in the hyperemic state; and (6) the CFD results corresponding to the image data may be registered based on the deformation field, so that one of the second sample and the fourth sample may be quickly determined, thereby reducing the amount of computation.

Certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

It is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A system for determining hemodynamic parameters, comprising:

at least one storage medium including a set of instructions;

at least one processor in communication with the at least one storage medium, wherein when executing the set of instructions, the at least one processor is directed to cause the system to perform operations including:

obtaining image data of a subject being acquired in a rest state;

obtaining a trained machine learning model; and determining, based on the trained machine learning model, at least one target hemodynamic parameter of the subject, wherein the trained machine learning model is obtained based on multiple sets of sample image data, each set of the multiple sets of sample image data includes a first image data and at least one of a second image data or a third image data, the first image data is acquired in a rest state of a first sample subject, the second image data is acquired in a hyperemic state of the first sample subject, and the third image data is acquired in a hyperemic state of a second sample subject associated with the first sample subject.

2. The system of claim 1, where the determining, based on the trained machine learning model, at least one hemodynamic parameter of the subject includes:

determining, based on the image data of the subject, a structure model of the subject; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject;

determining one or more boundary conditions associated with the subject; and determining the at least one target hemodynamic parameter of the subject by inputting the structure model, and the one or more boundary conditions into the trained machine learning model.

3. The system of claim 1, where the determining, based on the trained machine learning model, at least one hemodynamic parameter of the subject includes:

determining the at least one target hemodynamic parameter of the subject by inputting the image data of the subject into the trained machine learning model; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject.

4. The system of claim 1, where the trained machine learning model is obtained based on multiple groups of training samples, training samples in each group are determined based on one set of the multiple sets of sample image data, a training sample in each group includes a computational fluid dynamics (CFD) result determined based on the first image data, or the second image data, or the third image data and the first image data, or the third image data and the second image data, and a reference hemodynamic parameter corresponding to the CFD result.

5. The system of claim 4, wherein the training samples in each group include a first sample and at least one of a second sample, a third sample, or a fourth sample, the first sample includes a first CFD result determined based on the first image data;

the second sample includes a second CFD result determined based on the second image data;

the third sample includes a third CFD result determined based on the first image data and the third image data; and the fourth sample includes a fourth CFD result determined based on the second image data and the third image data.

6. The system of claim 5, where the first sample is obtained according to operations including:

determining, based on the first image data, a first structure model representing the first sample subject;

determining, based on the first structure model, one or more first boundary conditions of the first sample subject; and determining, based on the one or more first boundary conditions and the first structure model, the first CFD result.

7. The system of claim 5, where the second sample is obtained according to operations including:

determining, based on the second image data, a second structure model representing the first sample subject;

determining, based on the second structure model or the second image data, one or more second boundary conditions of the first sample subject; and determining, based on the one or more second boundary conditions and the second structure model, the second CFD result.

8. The system of claim 7, wherein the determining, based on the second image data, a second structure model representing the first sample subject includes:

obtaining a second trained machine learning model; and determining the second structure model representing the first sample subject in the hyperemic state using the second trained machine learning model.

9. The system of claim 5, wherein the third sample is obtained according to operations including:

determining, based on the first image data, a first structure model representing the first sample subject;

determining, based on the third image data, one or more third boundary conditions of the first sample subject; and determining, based on the one or more third boundary conditions and the first structure model, the third CFD result.

10. The system of claim 9, wherein the determining, based on the third image data, one or more third boundary conditions of the first sample subject includes:

determining a first region from the first image data;

determining a parametric image representing functional indexes of different portions of the first sample subject based on the third image data;

determining a second region in the first region from the parametric image by registering the parametric image with the first image data; and determining, based on the second region, the one or more third boundary conditions.

11. The system of claim 5, wherein the fourth sample is obtained according to operations including:

determining, based on the second image data, a second structure model representing the first sample subject;

determining, based on the third image data, one or more third boundary conditions of the first sample subject; and determining, based on the one or more third boundary conditions and the second structure model, the fourth CFD result.

12. The system of claim 5, wherein the second sample or the fourth sample is obtained according to operations including:

for one of the second sample and the fourth sample;

registering the second image data with the first image data to obtain a deformation field; and obtaining the one of the second sample and the fourth image based on the deformation field.

13. A system for determining hemodynamic parameters, comprising:

at least one storage medium including a set of instructions;

at least one processor in communication with the at least one storage medium, wherein when executing the set of instructions, the at least one processor is directed to cause the system to perform operations including:

obtaining first image data of a subject being acquired in a rest state;

obtaining second image data of the subject acquired in a hyperemic state;

determining, based on the first image data, a structure model representing the subject;

determining, based on the second image data, one or more boundary conditions of the subject; and determining, based on the one or more boundary conditions and the structure model, at least one target hemodynamic parameter of the subject.

14. A method for determining hemodynamic parameters, comprising:

obtaining image data of a subject being acquired in a rest state;

obtaining a trained machine learning model; and determining, based on the trained machine learning model, at least one target hemodynamic parameter of the subject, wherein the trained machine learning model is obtained based on multiple sets of sample image data, each set of the multiple sets of sample image data includes a first image data and at least one of a second image data or a third image data, the first image data is acquired in a rest state of a first sample subject, the second image data is acquired in a hyperemic state of the first sample subject, and the third image data is acquired in a hyperemic state of a second sample subject associated with the first sample subject.

15. The method of claim 14, where the determining, based on the trained machine learning model, at least one hemodynamic parameter of the subject includes:

determining, based on the image data of the subject, a structure model of the subject; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject;

determining one or more boundary conditions associated with the subject; and determining the at least one target hemodynamic parameter of the subject by inputting the structure model, and the one or more boundary conditions into the trained machine learning model.

16. The method of claim 14, where the determining, based on the trained machine learning model, at least one hemodynamic parameter of the subject includes:

determining the at least one target hemodynamic parameter of the subject by inputting the image data of the subject into the trained machine learning model; the image data of the subject includes the first image data and at least one of the second image data or the third image data, the first image data is acquired in a rest state of the first sample subject, the second image data is acquired in a hyperemic state of the first sample subject, and the third image data is acquired in a hyperemic state of a second sample subject associated with the first sample subject.

17. The method of claim 14, where the trained machine learning model is obtained based on multiple groups of training samples, training samples in each group are determined based on one set of the multiple sets of sample image data, a training sample in each group includes a computational fluid dynamics (CFD) result determined based on the first image data, or the second image data, or the third image data and the first image data, or the third image data and the second image data, and a reference hemodynamic parameter corresponding to the CFD result.

18. The method of claim 17, wherein the training samples in each group include a first sample and at least one of a second sample, a third sample, or a fourth sample, the first sample includes a first CFD result determined based on the first image data;

the second sample includes a second CFD result determined based on the second image data;

the third sample includes a third CFD result determined based on the first image data and the third image data; and the fourth sample includes a fourth CFD result determined based on the second image data and the third image data.

19. The method of claim 18, where the first sample is obtained according to operations including:

determining, based on the first image data, a first structure model representing the first sample subject;

determining, based on the first structure model, one or more first boundary conditions of the first sample subject; and determining, based on the one or more first boundary conditions and the first structure model, the first CFD result.

20. The method of claim 18, where the second sample is obtained according to operations including:

determining, based on the second image data, a second structure model representing the first sample subject;

determining, based on the second structure model or the second image data, one or more second boundary conditions of the first sample subject; and determining, based on the one or more second boundary conditions and the second structure model, the second CFD result.

* * * * *